United States Patent
Stahmann et al.

(10) Patent No.: US 11,260,216 B2
(45) Date of Patent: Mar. 1, 2022

(54) METHODS AND SYSTEMS FOR DETECTING ATRIAL CONTRACTION TIMING FIDUCIALS DURING VENTRICULAR FILLING FROM A VENTRICULARLY IMPLANTED LEADLESS CARDIAC PACEMAKER

(71) Applicant: CARDIAC PACEMAKERS, INC., St. Paul, MN (US)

(72) Inventors: Jeffrey E. Stahmann, Ramsey, MN (US); Keith R. Maile, New Brighton, MN (US); Krzysztof Z. Siejko, Maple Grove, MN (US); Allan Charles Shuros, St. Paul, MN (US); William J. Linder, Golden Valley, MN (US); Benjamin J. Haasl, Forest Lake, MN (US); Michael J. Kane, St. Paul, MN (US); Brendan Early Koop, Ham Lake, MN (US)

(73) Assignee: CARDIAC PACEMAKERS, INC., St. Paul, MN (US)

(*) Notice: Subject to any disclaimer, the term of this patent is extended or adjusted under 35 U.S.C. 154(b) by 130 days.

(21) Appl. No.: 16/201,678

(22) Filed: Nov. 27, 2018

(65) Prior Publication Data
US 2019/0167972 A1 Jun. 6, 2019

Related U.S. Application Data

(60) Provisional application No. 62/593,642, filed on Dec. 1, 2017.

(51) Int. Cl.
*A61N 1/02* (2006.01)
*A61N 1/372* (2006.01)
(Continued)

(52) U.S. Cl.
CPC ............ *A61N 1/025* (2013.01); *A61N 1/059* (2013.01); *A61N 1/36507* (2013.01);
(Continued)

(58) Field of Classification Search
CPC .... A61N 1/025; A61N 1/059; A61N 1/36507; A61N 1/36521; A61N 1/36528;
(Continued)

(56) References Cited

U.S. PATENT DOCUMENTS 3,835,864 A 9/1974 Rasor et al.
3,943,936 A 3/1976 Rasor et al.
(Continued)

FOREIGN PATENT DOCUMENTS

AU 2008279789 B2 10/2011
AU 2008329620 B2 5/2014
(Continued)

OTHER PUBLICATIONS

US 8,886,318 B2, 11/2014, Jacobson et al. (withdrawn)
(Continued)

*Primary Examiner* — Jonathan T Kuo
(74) *Attorney, Agent, or Firm* — Seager, Tufte & Wickhem LLP.

(57) ABSTRACT

A ventricularly implantable medical device that includes a sensing module that is configured to detect an artifact during ventricular filling and to identify an atrial event based at least on part on the detected artifact. Control circuitry of the implantable medical device is configured to deliver a ventricular pacing therapy to a patient's heart, wherein the ventricular pacing therapy is time dependent, at least in part, on the identified atrial event.

20 Claims, 18 Drawing Sheets

(51) Int. Cl.
*A61N 1/375* (2006.01)
*A61N 1/05* (2006.01)
*A61N 1/365* (2006.01)

(52) U.S. Cl.
CPC ..... *A61N 1/36521* (2013.01); *A61N 1/36564* (2013.01); *A61N 1/36578* (2013.01); *A61N 1/36585* (2013.01); *A61N 1/3756* (2013.01); *A61N 1/37205* (2013.01); *A61N 1/37512* (2017.08); *A61N 1/36528* (2013.01); *A61N 1/36535* (2013.01); *A61N 1/36542* (2013.01); *A61N 1/36571* (2013.01)

(58) Field of Classification Search
CPC ............ A61N 1/36535; A61N 1/36542; A61N 1/36564; A61N 1/36571; A61N 1/36578; A61N 1/36585; A61N 1/37205; A61N 1/37512; A61N 1/3756; A61N 1/362–1/3688
See application file for complete search history.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,374,281 A * | 12/1994 | Kristall ............. A61N 1/36514 607/17 |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,441,489 A | 8/1995 | Utsumi et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |

(56) References Cited

U.S. PATENT DOCUMENTS

| | | |
|---|---|---|
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,066,126 A | 5/2000 | Li et al. |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |

(56) References Cited

U.S. PATENT DOCUMENTS

| | | |
|---|---|---|
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |

(56) References Cited

U.S. PATENT DOCUMENTS

| | | |
|---|---|---|
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |

(56) References Cited

U.S. PATENT DOCUMENTS

| | | |
|---|---|---|
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,080,887 B2 | 9/2018 | Schmidt et al. |
| 10,080,888 B2 | 9/2018 | Kelly et al. |
| 10,080,900 B2 | 9/2018 | Ghosh et al. |
| 10,080,903 B2 | 9/2018 | Willis et al. |
| 10,086,206 B2 | 10/2018 | Sambelashvili |
| 10,118,026 B2 | 11/2018 | Grubac et al. |
| 10,124,163 B2 | 11/2018 | Ollivier et al. |
| 10,124,175 B2 | 11/2018 | Berthiaume et al. |
| 10,130,821 B2 | 11/2018 | Grubac et al. |
| 10,137,305 B2 | 11/2018 | Kane et al. |
| 10,201,710 B2 | 2/2019 | Jackson et al. |
| 10,207,115 B2 | 2/2019 | Echt et al. |
| 10,207,116 B2 | 2/2019 | Sheldon et al. |
| 10,226,197 B2 | 3/2019 | Reinke et al. |
| 10,226,639 B2 | 3/2019 | Zhang |
| 10,232,182 B2 | 3/2019 | Hareland et al. |
| 10,265,503 B2 | 4/2019 | Schmidt et al. |
| 10,265,534 B2 | 4/2019 | Greenhut et al. |
| 10,271,752 B2 | 4/2019 | Regnier et al. |
| 10,278,601 B2 | 5/2019 | Greenhut et al. |
| 10,279,165 B2 | 5/2019 | Seifert et al. |
| 10,286,221 B2 | 5/2019 | Sawchuk |
| 10,307,598 B2 | 6/2019 | Ciciarelli et al. |
| 10,328,274 B2 | 6/2019 | Zhang et al. |
| 10,342,981 B2 | 7/2019 | Ghosh et al. |
| 10,441,793 B2 * | 10/2019 | Muessig ............ A61N 1/36514 |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |

(56) References Cited

U.S. PATENT DOCUMENTS

| | | |
|---|---|---|
| 2002/0095196 A1 | 7/2002 | Linberg |
| 2002/0099423 A1 | 7/2002 | Berg et al. |
| 2002/0103454 A1 | 8/2002 | Sackner et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0120337 A1 | 6/2003 | Van Tassel et al. |
| 2003/0144701 A1 | 7/2003 | Mehra et al. |
| 2003/0187460 A1 | 10/2003 | Chin et al. |
| 2003/0187461 A1 | 10/2003 | Chin |
| 2003/0191526 A1 | 10/2003 | Van Tassel et al. |
| 2003/0195572 A1 | 10/2003 | Bocek et al. |
| 2003/0204145 A1 | 10/2003 | Manolas |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0137634 A1 | 6/2005 | Hall et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0155338 A1 | 7/2006 | Mongeon et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0228452 A1 | 10/2006 | Cromack et al. |
| 2006/0228453 A1 | 10/2006 | Cromack et al. |
| 2006/0240070 A1 | 10/2006 | Cromack et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2006/0293715 A1 | 12/2006 | Plicchi et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0060787 A1 | 3/2007 | Peters et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0093874 A1* | 4/2007 | Chirife .................. A61N 1/368 607/25 |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0179541 A1 | 8/2007 | Prakash et al. |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239210 A1 | 10/2007 | Libbus et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0009791 A1 | 1/2008 | Cohen et al. |
| 2008/0009910 A1 | 1/2008 | Kraetschmer et al. |
| 2008/0010024 A1 | 1/2008 | Diamond |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294217 A1 | 11/2008 | Lian et al. |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |

(56) References Cited

U.S. PATENT DOCUMENTS

| | | |
|---|---|---|
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088648 A1 | 4/2009 | Jaffe et al. |
| 2009/0088813 A1 | 4/2009 | Brockway et al. |
| 2009/0112285 A1 | 4/2009 | Cahan et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0149908 A1 | 6/2009 | Bjorling et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0216317 A1 | 8/2009 | Cromack et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299424 A1 | 12/2009 | Narayan |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094274 A1 | 4/2010 | Narayan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0131027 A1 | 5/2010 | Sathaye et al. |
| 2010/0168761 A1 | 7/2010 | Kassab et al. |
| 2010/0168819 A1 | 7/2010 | Freeberg |
| 2010/0174333 A1 | 7/2010 | Dewals |
| 2010/0198288 A1 | 8/2010 | Ostroff |
| 2010/0198289 A1 | 8/2010 | Kameli et al. |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0268040 A1 | 10/2010 | Ben-Oren et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0098769 A1* | 4/2011 | Betzold .............. A61N 1/36507 607/25 |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0202099 A1 | 8/2011 | Makdissi |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0065597 A1 | 3/2012 | Cohen |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0090702 A1 | 4/2013 | Mongeon et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |

(56) References Cited

U.S. PATENT DOCUMENTS

| | | |
|---|---|---|
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0131750 A1 | 5/2013 | Stadler et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0204312 A1 | 8/2013 | Gill et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018690 A1 | 1/2014 | Carlson et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094676 A1 | 4/2014 | Gani et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228696 A1 | 8/2014 | Narayan et al. |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0277237 A1 | 9/2014 | Maskara et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0031966 A1 | 1/2015 | Ward et al. |
| 2015/0038962 A1 | 2/2015 | Cohen |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0112425 A1 | 4/2015 | Cromack et al. |
| 2015/0126854 A1 | 5/2015 | Keast et al. |
| 2015/0142069 A1 | 5/2015 | Sambelashvili |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335383 A9 | 11/2015 | Cohen |
| 2015/0335884 A1 | 11/2015 | Khairkhahan et al. |
| 2015/0342466 A1 | 12/2015 | Thakur et al. |
| 2015/0360041 A1 | 12/2015 | Stahmann et al. |
| 2016/0015322 A1 | 1/2016 | Anderson et al. |

(56) References Cited

U.S. PATENT DOCUMENTS

| | | |
|---|---|---|
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0051823 A1 | 2/2016 | Maile et al. |
| 2016/0067486 A1 | 3/2016 | Brown et al. |
| 2016/0114161 A1 | 4/2016 | Amblard et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0144192 A1 | 5/2016 | Sanghera et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0262691 A1 | 9/2016 | Jain et al. |
| 2016/0270734 A1 | 9/2016 | Imhoff et al. |
| 2016/0278657 A1 | 9/2016 | Narayan et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0027458 A1 | 2/2017 | Glover et al. |
| 2017/0028203 A1 | 2/2017 | Ghosh |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0274213 A1 | 9/2017 | Ghosh et al. |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2017/0368347 A1* | 12/2017 | Muessig ............... A61N 1/3622 |
| 2018/0008829 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0339160 A1 | 11/2018 | Carroll |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2471452 A1 | 7/2012 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2005000206 A3 | 1/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |
| WO | 2013184787 A1 | 12/2013 |
| WO | 2014120769 A1 | 8/2014 |
| WO | 2016014352 A1 | 1/2016 |

OTHER PUBLICATIONS

International Search Report and Written Opinion for Application No. PCT/US2018/063122, 14 pages, dated Feb. 14, 2019.

International Search Report and Written Opinion for Application No. PCT/US2018/062469, 12 pages, dated Feb. 26, 2019.

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Spickler et al., "Totally Self-Contained Intracardiac Pacemaker," Journal of Electrocardiology, vol. 3(3&4): 324-331, 1970.

Wegmüller, "Intra-Body Communication for Biomedical Sensor Networks," Diss. ETH, No. 17323, 1-173, 2007.

Chinitz et al.; "Accelerometer-Based Atrioventricular Synchronus Pacing with a Ventricular Leadless Pacemaker Results from the Micra Atrioventricular Feasibility Studies", Heart Rhythm 15, pp. 1363-1371, 2018.

International Search Report and Written Opinion for Application No. PCT/US2018/062631, 13 pages, dated Feb. 5, 2019.

* cited by examiner

| Sensor Modality | P Wave | A Wave | S1 | S2 | S3 | S4 | Ventricular Volume | Ventricular Wall Dimension | Cardiac Tissue/Blood Vibration | Atrium to Ventricle Blood Movement | Ventricular wall / AV Valve Position | Akinetic Pressure | Ventricular Twist |
|---|---|---|---|---|---|---|---|---|---|---|---|---|---|
| Voltage | X | | | | | | | | | | | | |
| Pressure | | X | X | X | X | X | | | | | | X | |
| Sound | | | X | X | X | X | | | | | | | |
| Ultrasound | | | | | | | X | X | | X | X | | |
| Impedance | | | | | | | X | | | | | | |
| Strain | | | | | | | | X | | | | | |
| Acceleration | | | X | X | X | X | | | X | | | | |
| Flow | | | | | | | | | | X | | | |
| Rotation | | | | | | | | | | | | | X |

| Cardiac Phase | Measured Artifact | | | | | | | | | |
|---|---|---|---|---|---|---|---|---|---|---|
| | P Wave | A Wave | S1 | S2 | S3 | S4 | Ventricular Volume | Ventricular Wall Dimension | Cardiac Tissue/ Blood Vibration | Atrium to Ventricle Blood Movement | Ventricular wall / AV Valve Position | Akinetic Pressure | Ventricular Twist |
| Passive Ventricular Filling | X | | | | X | | X | X | | X | X | X | |
| Active Ventricular Filling | X | X | X | | | X | X | X | X | X | X | | |

(330)

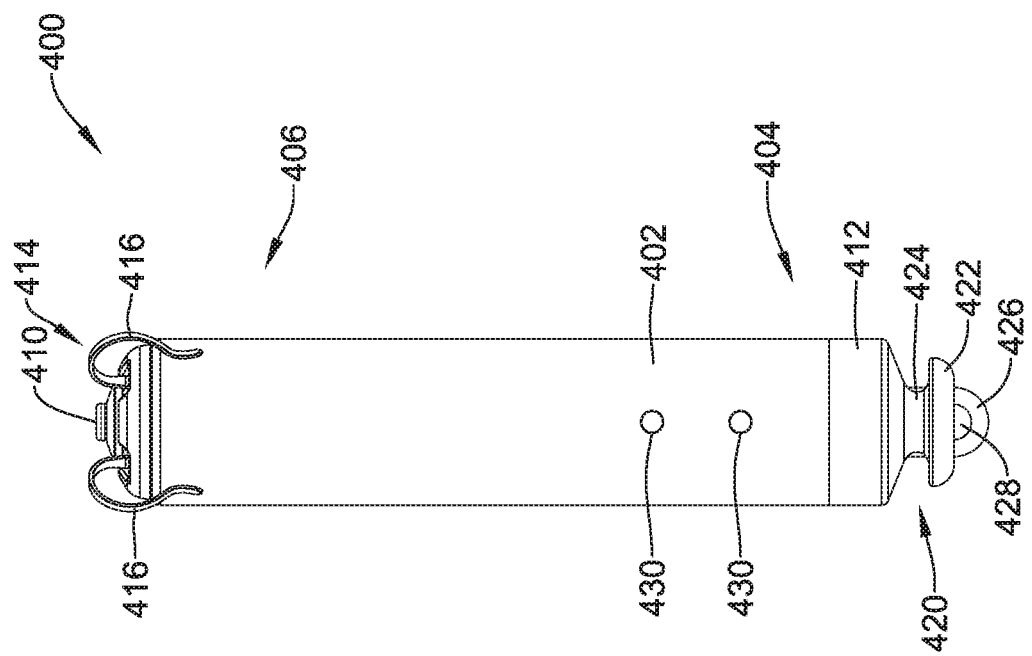

METHODS AND SYSTEMS FOR DETECTING ATRIAL CONTRACTION TIMING FIDUCIALS DURING VENTRICULAR FILLING FROM A VENTRICULARLY IMPLANTED LEADLESS CARDIAC PACEMAKER

CROSS REFERENCE TO RELATED APPLICATIONS

This application claims the benefit of U.S. Provisional Patent Application Ser. No. 62/593,642 filed on Dec. 1, 2017, the disclosure of which is incorporated herein by reference.

TECHNICAL FIELD

The present disclosure generally relates to implantable medical devices, and more particularly, to systems that use a leadless cardiac pacemaker for monitoring, pacing and/or defibrillating a patient's heart

BACKGROUND

Implantable medical devices are commonly used today to monitor a patient and/or deliver therapy to a patient. For example, and in some instances, pacing devices are used to treat patients suffering from various heart conditions that may result in a reduced ability of the heart to deliver sufficient amounts of blood to a patient's body. Such heart conditions may lead to slow, rapid, irregular, and/or inefficient heart contractions. To help alleviate some of these conditions, various medical devices (e.g., pacemakers, defibrillators, etc.) can be implanted in a patient's body. Such devices may monitor and in some cases provide electrical stimulation (e.g. pacing, defibrillation, etc.) to the heart to help the heart operate in a more normal, efficient and/or safe manner. In some cases, it may be beneficial to detect cardiac events occurring in multiple chambers of the heart. In some cases, this may be used to enhance the effectiveness of the cardiac pacing therapy and/or may allow different types of cardiac pacing therapy to be delivered.

SUMMARY

This disclosure generally relates to implantable medical devices, and more particularly, to systems that use a leadless cardiac pacemaker for monitoring, pacing and/or defibrillating a patient's heart.

In a first example, a leadless cardiac pacemaker (LCP) may be configured to sense cardiac activity and to deliver pacing therapy to a ventricle of a patient's heart. The LCP may comprise a housing having a proximal end and a distal end, a first electrode secured relative to the housing and exposed to the environment outside of the housing, a second electrode secured relative to the housing and exposed to the environment outside of the housing, a sensing module disposed within the housing, the sensing module configured to detect an artifact during ventricular filling and identify an atrial event based, at least in part, on the detected artifact, and circuitry in the housing operatively coupled to the first electrode and the second electrode, and also operatively coupled to the sensing module, the circuitry configured to deliver a ventricular pacing therapy to the patient's heart via the first electrode and the second electrode, wherein the ventricular pacing therapy is time dependent, at least in part, on the identified atrial event.

Alternatively or additionally to any of the examples above, in another example, the sensing module may be configured to detect an atrial artifact during passive ventricular filling.

Alternatively or additionally to any of the examples above, in another example, the sensing module may be configured to sense at least one of a pressure, impedance, strain, sound, rotation, acceleration, voltage, and flow.

Alternatively or additionally to any of the examples above, in another example, the sensing module may comprise a filter for filtering a signal for the at least one of pressure, impedance, strain, sound, rotation, acceleration, voltage, and flow.

Alternatively or additionally to any of the examples above, in another example, the filter may include a first filter for passing a first frequency band, a second filter for passing a second frequency band and a third filter for passing a third frequency band.

Alternatively or additionally to any of the examples above, in another example, the artifact may comprise at least one of a p-wave, S2 heart sound, S3 heart sound, ventricular volume, ventricular wall dimension, ventricular blood movement, ventricular wall movement, tricuspid valve position, mitral valve position, and akinetic ventricular pressure.

Alternatively or additionally to any of the examples above, in another example, the sensing module may be configured to detect an atrial artifact during active ventricular filling.

Alternatively or additionally to any of the examples above, in another example, the sensing module may be configured to sense at least one of an impedance, strain, sound, rotation, or flow.

Alternatively or additionally to any of the examples above, in another example, the artifact may comprise at least one of a p-wave, a-wave, e-wave, S1 heart sound, S4 heart sound, ventricular volume, ventricular wall dimension, cardiac tissue vibration, ventricular blood movement, ventricular wall movement, tricuspid valve position, and mitral valve position.

Alternatively or additionally to any of the examples above, in another example, the sensing module may comprise a bandpass filter of about 1 Hertz (Hz) to about 5 Hz.

Alternatively or additionally to any of the examples above, in another example, the sensing module may comprise a bandpass filter of about 15 Hertz (Hz) to about 30 Hz.

Alternatively or additionally to any of the examples above, in another example, the sensing module may be further configured to detect at least one of posture, activity, or respiration.

Alternatively or additionally to any of the examples above, in another example, the circuitry may be further configured to determine an intrinsic interval based, at least in part, on the atrial event.

Alternatively or additionally to any of the examples above, in another example, the sensing module may be configured to calculate an ensemble average timing over multiple heart beats for the detected artifact.

Alternatively or additionally to any of the examples above, in another example, the LCP may be configured to be implantable in a ventricle of the patient's heart.

Alternatively or additionally to any of the examples above, in another example, the sensing module may be configured to detect an atrial artifact by detecting a transition between passive and active ventricular filling.

In another example, a leadless cardiac pacemaker (LCP) may be configured to sense cardiac activity and to deliver pacing therapy to a ventricle of a patient's heart. The LCP may comprise a housing having a proximal end and a distal end, a first electrode secured relative to the housing and exposed to the environment outside of the housing, a second electrode secured relative to the housing and exposed to the environment outside of the housing, a sensing module disposed within the housing, the sensing module configured to detect an artifact during ventricular filling and identify an atrial event based, at least in part, on the detected artifact, and circuitry in the housing operatively coupled to the first electrode and the second electrode, and also operatively coupled to the sensing module, the circuitry configured to deliver a ventricular pacing therapy to the patient's heart via the first electrode and the second electrode, wherein the ventricular pacing therapy is time dependent, at least in part, on the identified atrial event.

Alternatively or additionally to any of the examples above, in another example, the sensing module may be configured to detect an atrial artifact during passive ventricular filling.

Alternatively or additionally to any of the examples above, in another example, the sensing module may be configured to sense at least one of a pressure, impedance, strain, sound, rotation, acceleration, voltage, and flow.

Alternatively or additionally to any of the examples above, in another example, the artifact may comprise at least one of a p-wave, S2 heart sound, S3 heart sound, ventricular volume, ventricular wall dimension, ventricular blood movement, ventricular wall movement, tricuspid valve position, mitral valve position, and akinetic ventricular pressure.

Alternatively or additionally to any of the examples above, in another example, the sensing module may be configured to detect an atrial artifact during active ventricular filling.

Alternatively or additionally to any of the examples above, in another example, the sensing module may be configured to sense at least one of an impedance, strain, sound, rotation, or flow.

Alternatively or additionally to any of the examples above, in another example, the artifact may comprise at least one of p-wave, a-wave, e-wave, S1 heart sound, S4 heart sound, ventricular volume, ventricular wall dimension, cardiac tissue vibration, ventricular blood movement, ventricular wall movement, tricuspid valve position, and mitral valve position.

Alternatively or additionally to any of the examples above, in another example, the sensing module may be further configured to detect at least one of posture, activity, or respiration.

Alternatively or additionally to any of the examples above, in another example, the sensing module may be configured to detect an atrial artifact by detecting a transition between passive and active ventricular filling.

Alternatively or additionally to any of the examples above, in another example, the circuitry may be further configured to determine an intrinsic interval based, at least in part, on the atrial event.

In another example, an implantable medical device may be configured to sense cardiac activity and to deliver pacing therapy to a patient's heart. The implantable medical device may comprise a housing, a first electrode secured relative to the housing and exposed to the environment outside of the housing, a second electrode secured relative to the housing and exposed to the environment outside of the housing, and a sensing module disposed within the housing. The sensing module may be configured to sense during passive ventricular filling of the patient's heart at least one of a pressure, impedance, strain, sound, rotation, acceleration, voltage, and flow, detect an artifact, and identify an atrial event based, at least in part, on the detected artifact. The implantable medical device may further comprise circuitry in the housing operatively coupled to the first electrode, the second electrode, and the sensing module, the circuitry configured to deliver a ventricular pacing pulse to the patient's heart via the first electrode and the second electrode, wherein a timing of the ventricular pacing pulse is dependent, at least in part, on the timing of the identified atrial event.

Alternatively or additionally to any of the examples above, in another example, the sensing module may comprise a filter for filtering a signal for the at least one of pressure, impedance, strain, sound, rotation, acceleration, voltage, and flow.

Alternatively or additionally to any of the examples above, in another example, the filter may include a first filter for passing a first frequency band, a second filter for passing a second frequency band and a third filter for passing a third frequency band.

Alternatively or additionally to any of the examples above, in another example, the sensing module may be configured to calculate an ensemble average timing over multiple heart beats for the detected artifact.

Alternatively or additionally to any of the examples above, in another example, the detected artifact may comprise at least one of a p-wave, S2 heart sound, S3 heart sound, ventricular volume, ventricular wall dimension, ventricular blood movement, ventricular wall movement, tricuspid valve position, mitral valve position, and akinetic ventricular pressure.

Alternatively or additionally to any of the examples above, in another example, the implantable medical device may be configured to be implantable in a ventricle of the patient's heart and the sensing module identifies an atrial event based, at least in part, on the detected artifact.

In another example, an implantable medical device may be configured to sense cardiac activity and to deliver pacing therapy to a patient's heart. The implantable medical device may comprise a housing, a first electrode secured relative to the housing and exposed to the environment outside of the housing, a second electrode secured relative to the housing and exposed to the environment outside of the housing, and a sensing module disposed within the housing. The sensing module may be configured to sense during active ventricular filling of the patient's heart at least one of a pressure, impedance, strain, sound, rotation, acceleration, voltage, and flow, detect an artifact, and identify an atrial event based, at least in part, on the detected artifact. The implantable medical device may further comprise circuitry in the housing operatively coupled to the first electrode, the second electrode, and the sensing module, the circuitry is configured to deliver a ventricular pacing therapy to the patient's heart via the first electrode and the second electrode, wherein the ventricular pacing therapy is time dependent, at least in part, on the identified atrial event.

Alternatively or additionally to any of the examples above, in another example, the sensing module may comprise a bandpass filter of about 1 Hertz (Hz) to about 5 Hz.

Alternatively or additionally to any of the examples above, in another example, the sensing module may comprise a bandpass filter of about 15 Hertz (Hz) to about 30 Hz.

Alternatively or additionally to any of the examples above, in another example, the artifact may comprise at least one of a p-wave, a-wave, e-wave, S1 heart sound, S4 heart sound, ventricular volume, ventricular wall dimension, cardiac tissue vibration, ventricular blood movement, ventricular wall movement, tricuspid valve position, and mitral valve position.

Alternatively or additionally to any of the examples above, in another example, the implantable medical device may be configured to be implantable in a ventricle of the patient's heart and the sensing module identifies an atrial event based, at least in part, on the detected artifact.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIG. 6 is an illustrative table of various artifacts occurring during the cardiac cycle and different ways to detect them;

FIG. 7 is an illustrative table of various artifacts occurring during the cardiac cycle and during which cardiac phase each occur;

FIG. 8 is a side view of an illustrative LCP;

Figure 1:
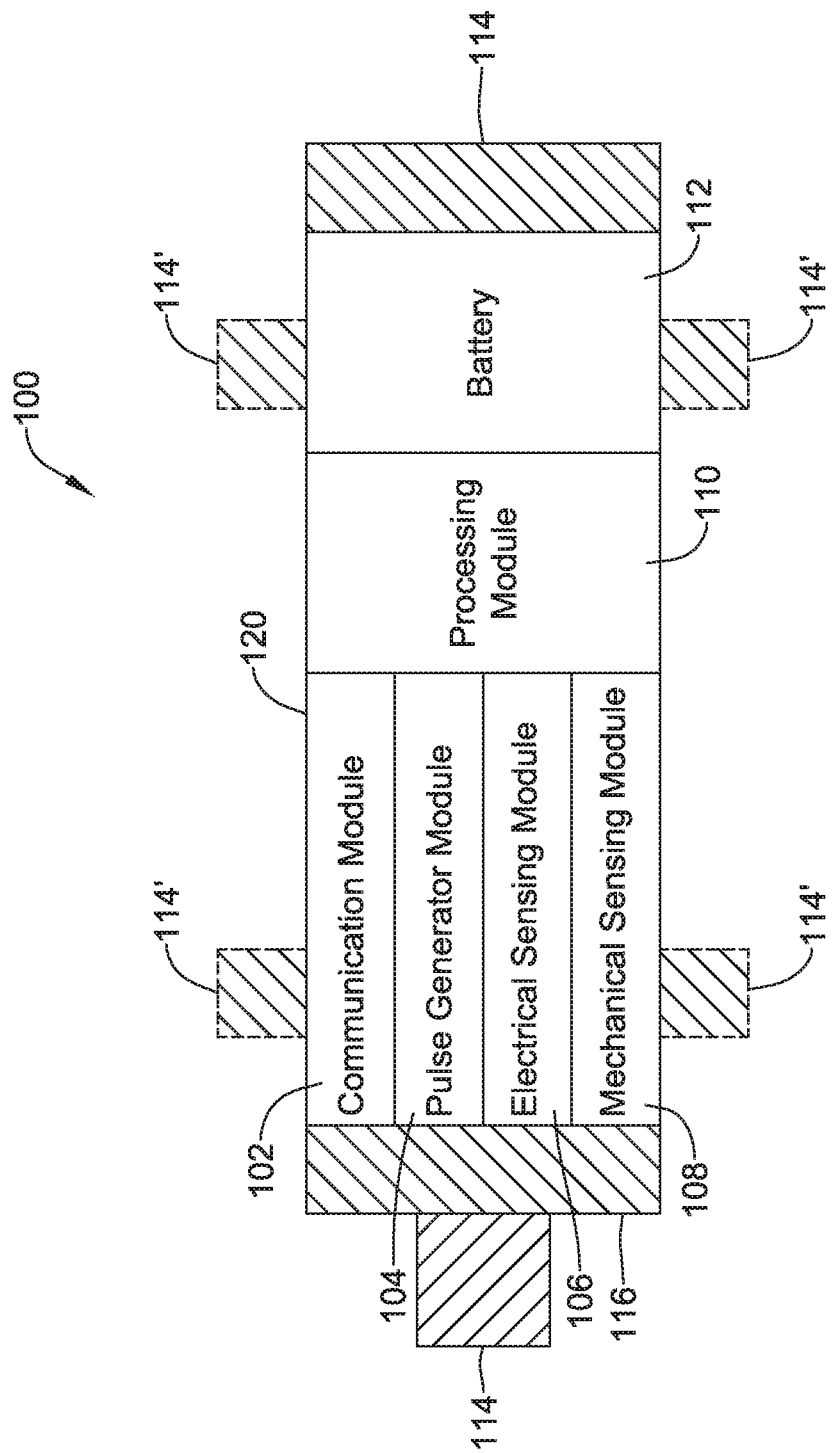
FIG. 1 is a schematic block diagram of an illustrative leadless cardiac pacemaker (LCP) according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure. While the present disclosure is applicable to any suitable implantable medical device (IMD), the description below uses pacemakers and more particularly leadless cardiac pacemakers (LCP) as particular examples.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

A normal, healthy heart induces contraction by conducting intrinsically generated electrical signals throughout the heart. These intrinsic signals cause the muscle cells or tissue of the heart to contract in a coordinated manner. These contractions force blood out of and into the heart, providing circulation of the blood throughout the rest of the body. Many patients suffer from cardiac conditions that affect the efficient operation of their hearts. For example, some hearts develop diseased tissue that no longer generate or efficiently conduct intrinsic electrical signals. In some examples, diseased cardiac tissue may conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate, even resulting in cardiac fibrillation. In some cases such an abnormality can develop into a fibrillation state, where the contraction of the patient's heart chambers are almost completely de-synchronized and the heart pumps very little to no blood. Implantable medical devices, which may be configured to determine occurrences of such cardiac abnormalities or arrhythmias and deliver one or more types of electrical stimulation therapy to patient's hearts, may help to terminate or alleviate these and other cardiac conditions.

It is contemplated that atrial events or artifacts indicative of an atrial event may be used by a device implanted in the right (or left) ventricle to time a pacing pulse for the ventricle in support of treating bradycardia events. In some cases, the timing of the ventricle pacing pulse may be adjusted to maximize the amount of blood entering the right ventricle through passive filling. In some instances, this may include adjusting an AV delay relative to an atrial fiducial (e.g., atrial kick). In some cases, a measured pressure change (or other atrial fiducial) over time may be used to support management of a CRT cardiac therapy (e.g. if placed in the left ventricle), patient health status monitoring and/or any other suitable goal. It is contemplated that measuring events in one of or both of the ventricle and atrium using a single leadless cardiac pacemaker may replicate a dual chamber system using only a single device. For example, such a system may enable a device to be positioned in a ventricle and capable of sensing intrinsic ventricular and atrial events and pacing the ventricle when appropriate (e.g., a VDD pacemaker).

FIG. 1 depicts an illustrative leadless cardiac pacemaker (LCP) that may be implanted into a patient to provide bradycardia therapy, cardiac resynchronization therapy (CRT), anti-tachycardia pacing (ATP) therapy, defibrillation therapy, and/or the like. As can be seen in FIG. 1, the illustrative LCP 100 may be a compact device with all components housed within and/or on the LCP housing 120. In the example shown in FIG. 1, the LCP 100 includes a communication module 102, a pulse generator module 104, an electrical sensing module 106, a mechanical sensing module 108, a processing module 110, a battery 112, and electrodes 114. It is contemplated that the LCP 100 may include more or less modules, depending on the application.

The communication module 102 may be configured to communicate with remote devices such as sensors, other devices, and/or the like, that are located externally and/or internally to the patient's body. The other devices may be device primarily functioning as a medical device (e.g. a LCP programmer, an implanted sensor) or a device primarily functioning as a non-medical device (e.g. a personal computer, tablet computer, smart phone, laptop computer or the like). Irrespective of the location or primary function, the remote devices (i.e., external to the LCP 100 but not necessarily external to the patient's body) may communicate with the LCP 100 via the communication module 102 to accomplish one or more desired functions. For example, the LCP 100 may communicate information, such as sensed signals, data, instructions, messages, etc., to a remote medical device through the communication module 102. The remote medical device may then use the communicated signals, data, instructions and/or messages to perform various functions, such as determining occurrences of arrhythmias, delivering electrical stimulation therapy, storing received data, analyzing received data, transmitting the received data to an external programmer or server or the like for review by a physician, and/or performing any other suitable function. The LCP 100 may additionally receive information such as signals, data, instructions and/or messages from the remote medical device through the communication module 102, and the LCP 100 may use the received signals, data, instructions and/or messages to perform various functions, such as determining occurrences of arrhythmias, delivering electrical stimulation therapy, storing received data, analyzing received data, and/or performing any other suitable function. The communication module 102 may be configured to use one or more methods for communicating with remote devices. For example, the communication module 102 may communicate via radiofrequency (RF) signals, inductive coupling, optical signals, acoustic signals, conducted communication signals, and/or any other signals suitable for communication.

In the example shown in FIG. 1, the pulse generator module 104 may be electrically connected to the electrodes 114. In some examples, the LCP 100 may include one or more additional electrodes 114'. In such examples, the pulse generator 104 may also be electrically connected to the additional electrodes 114'. The pulse generator module 104 may be configured to generate electrical stimulation signals. For example, the pulse generator module 104 may generate electrical stimulation signals by using energy stored in a battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) that the pulse generator 104 uses to deliver the electrical stimulation therapy. The pulse generator module 104 may generate electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac dyssynchrony, bradycardia arrhythmias, tachycardia arrhythmias, fibrillation arrhythmias, cardiac synchronization arrhythmias and/or to produce any other suitable electrical stimulation therapy. Some more common electrical stimulation therapies include bradycardia therapy, anti-tachycardia pacing (ATP) therapy, cardiac resynchronization therapy (CRT), and cardioversion/defibrillation therapy.

In some examples, the LCP 100 may not include a pulse generator 104 or may turn off the pulse generator 104. When so provided, the LCP 100 may be a diagnostic only device. In such examples, the LCP 100 may not deliver electrical stimulation therapy to a patient. Rather, the LCP 100 may collect data about cardiac electrical activity and/or other physiological parameters of the patient and communicate such data and/or determinations to one or more other medical devices via the communication module 102.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber (e.g. near field) in which the LCP 100 is implanted. For instance, if the LCP 100 is implanted within a ventricle of the heart, cardiac electrical signals sensed by the LCP 100 through the electrodes 114/114' may represent ventricular cardiac electrical signals, and possibly some weaker atrial electrical signals. The electrical sensing module 106 may be configured to detect voltage, current and/or impedance. An electrogram sensing module may be provided as a part of the electrical sensing module.

The mechanical sensing module 108 may include one or more sensors, such as an accelerometer, a gyroscope, a microphone, a hydrophone, a blood pressure sensor, a heart sound sensor, a blood-oxygen sensor, a temperature sensor, a flow sensor, a strain sensor, and/or any other suitable sensors that are configured to measure one or more mechanical and/or chemical parameters of the patient. In some cases, the mechanical sensing module 108 may include two or more of a pressure measurement module, an acoustic measurement module, an acceleration measurement module.

Both the electrical sensing module 106 and the mechanical sensing module 108 may be connected to a processing module 110, which may provide signals representative of the sensed mechanical parameters. Although described with respect to FIG. 1 as separate sensing modules, in some cases, the electrical sensing module 106 and the mechanical sensing module 108 may be combined into a single sensing module, as desired.

The electrodes 114/114' can be secured relative to the housing 120 but exposed to the tissue and/or blood surrounding the LCP 100. In some cases, the electrodes 114 may be generally disposed on or near either end of the LCP 100 and may be in electrical communication with one or more of the modules 102, 104, 106, 108, and 110. The electrodes 114/114' may be supported by the housing 120, although in some examples, the electrodes 114/114' may be secured relative to the housing 120 through short connecting wires (e.g. tail) such that one or more of the electrodes 114/114' may be spaced from the housing 120. In examples where the LCP 100 includes one or more electrodes 114', the electrodes 114' may in some cases be disposed on the sides of the housing 120 of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to LCP 100 may have an insulative portion that electrically isolates the electrodes 114/114' from adjacent electrodes, the housing 120, and/or other parts of the LCP 100.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, a need for pacing therapy such as bradycardia therapy, cardiac resynchronization therapy (CRT), anti-tachycardia pacing (ATP) therapy, defibrillation therapy, and/or the like. The processing module 110 may control the pulse generator module 104 to generate electrical stimulation in accordance with one or more pacing therapies. The processing module 110 may further receive information from the communication module 102. In some examples, the processing module 110 may use such received information to help determine the need for pacing therapy and/or what type of pacing therapy. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g., general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In still other examples, the battery 112 may be some other type of power source, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 2:
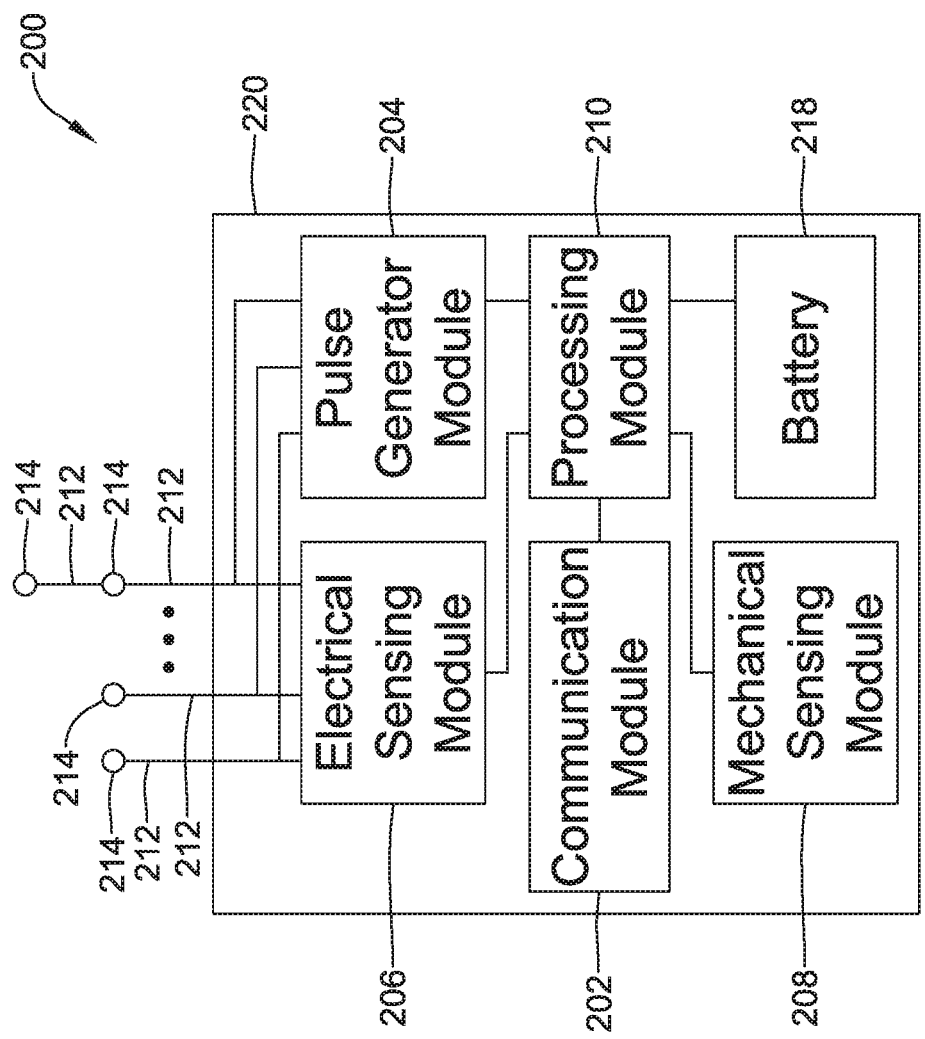
FIG. 2 a schematic block diagram of another medical device (MID), which may be used in conjunction with an LCP 100 (FIG. 1) in order to detect and/or treat cardiac arrhythmias and other heart conditions.

FIG. 2 depicts an example of another medical device (MD) 200, which may be used in conjunction with an LCP 100 (FIG. 1) in order to detect and/or treat cardiac arrhythmias and other heart conditions. In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of the LCP 100. Additionally, the battery 218 may be similar to the battery 112 of the LCP 100. In some examples, the MD 200 may have a larger volume within the housing 220 than LCP 100. In such examples, the MD 200 may include a larger battery and/or a larger processing module 210 capable of handling more complex operations than the processing module 110 of the LCP 100.

While it is contemplated that the MD 200 may be another leadless device such as shown in FIG. 1, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some of the leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned substernally or subcutaneously and spaced from but adjacent to the patient's heart. In some cases, the electrodes 214 may conduct intrinsically generated electrical signals to the leads 212, e.g., signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and deliver the signals to the patient's heart (either directly or indirectly).

The mechanical sensing module 208, as with the mechanical sensing module 108, may contain or be electrically connected to one or more sensors, such as microphones, hydrophones, accelerometers, gyroscopes, blood pressure sensors, heart sound sensors, blood-oxygen sensors, acoustic sensors, ultrasonic sensors, strain sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart or in concert with the LCP by commanding the LCP to pace. In some examples, the MD 200 may additionally be configured to provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In some instances, the MD 200 may be a subcutaneous implantable cardioverter-defibrillator (S-ICD). In examples where the MD 200 is an S-ICD, one of the leads 212 may be a subcutaneously or substernally implanted lead that is spaced from the heart. In at least some examples where the MD 200 is an S-ICD, the MD 200 may include only a single lead which is implanted subcutaneously or substernally, but this is not required. In some cases, the S-ICD lead may extend subcutaneously from the S-ICD can, around the sternum and may terminate adjacent the interior surface of the sternum and spaced from the heart.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g., cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy. The MD 200 may be further configured to deliver electrical stimulation via the LCP by commanding the LCP to deliver the therapy.

It is contemplated that one or more LCPs 100 and/or one or more MDs 200 may be used in combination as an example medical device system. The various devices 100, 200 may communicate through various communication pathways including using RF signals, inductive coupling, conductive coupling optical signals, acoustic signals, or any other signals suitable for communication. The system may further include and be in communication with a display. The display may be a personal computer, tablet computer, smart phone, laptop computer, or other display as desired. In some instances, the display may include input means for receiving an input from a user. For example, the display may also include a keyboard, mouse, actuatable (e.g., pushable) buttons, or a touchscreen display. These are just examples. Some illustrative medical device systems are described in commonly assigned Patent Application No. 62/547,458, entitled IMPLANTABLE MEDICAL DEVICE WITH PRESSURE SENSOR and filed on Aug. 18, 2017, which is hereby incorporated by reference.

Figure 3:
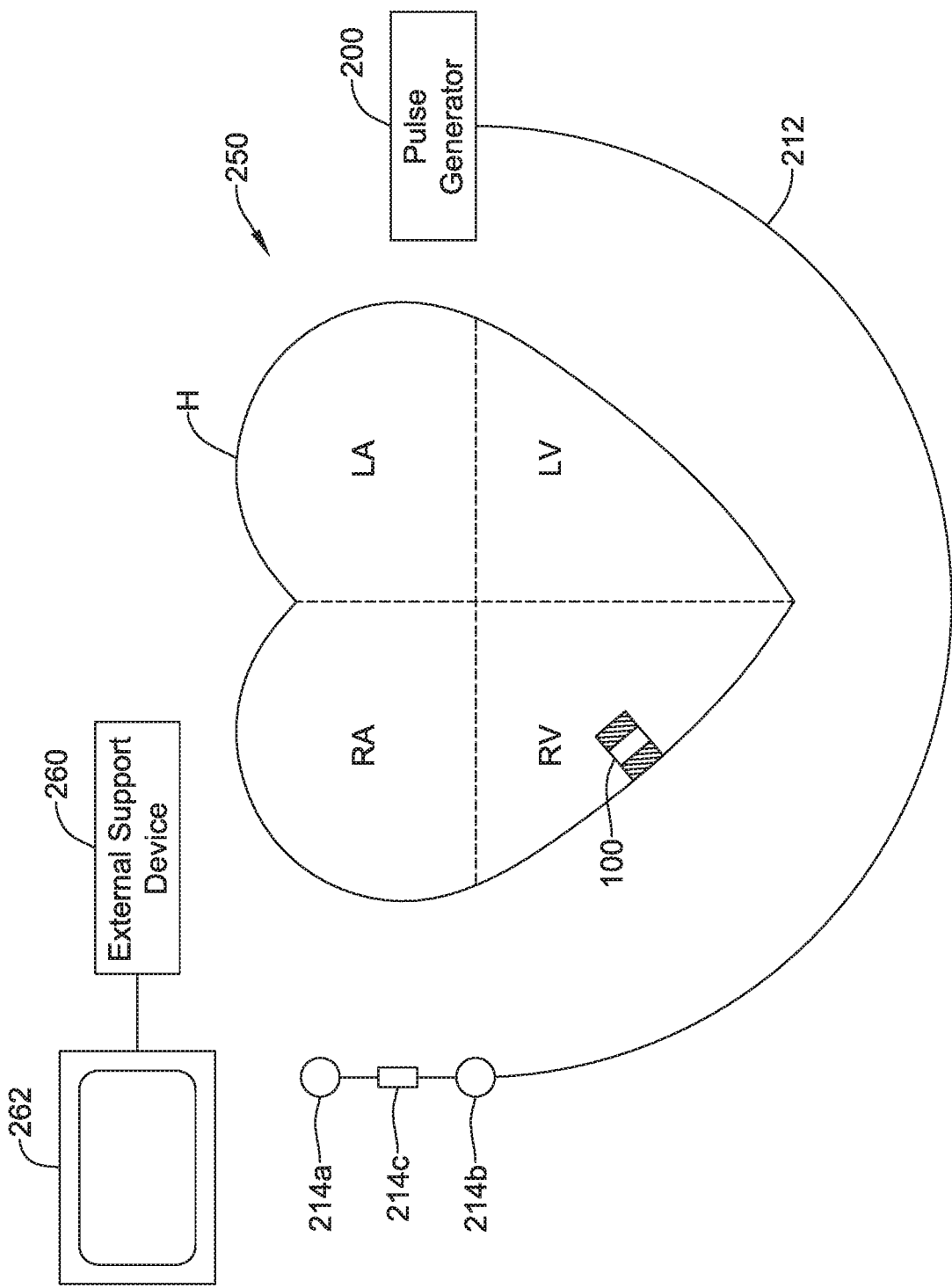
FIG. 3 is a schematic diagram of an exemplary medical system that includes an LCP and another medical device, in accordance with yet another example of the present disclosure.

FIG. 3 shows an example system 250 incorporating an LCP 100 and a MD 200. In FIG. 3, an LCP 100 is shown fixed to the interior of the right ventricle of the heart H, and MD 200 including a pulse generator is shown coupled to a lead 212 having one or more electrodes 214a, 214b, 214c. In some cases, the MD 200 may be part of a subcutaneous implantable cardioverter-defibrillator (S-ICD), and the one or more electrodes 214a, 214b, 214c may be positioned subcutaneously or substernally adjacent the heart. In some cases, the S-ICD lead may extend subcutaneously from the S-ICD can, around the sternum and one or more electrodes 214a, 214b, 214c may be positioned adjacent the interior surface of the sternum but spaced from the heart H. In some cases, the LCP 100 may communicate with the subcutaneous implantable cardioverter-defibrillator (S-ICD).

In some cases, the LCP 100 may be in the left ventricle, right atrium or left atrium of the heart, as desired. In some cases, more than one LCP 100 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart. Further, the LCP 100 may be used without the second MD 200.

The medical device system 250 may also include an external support device, such as external support device 260. The external support device 260 can be used to perform functions such as device identification, device programming and/or transfer of real-time and/or stored data between devices using one or more of the communication techniques described herein. As one example, communication between the external support device 260 and the MD 200 is performed via a wireless mode (e.g. RF, Bluetooth, inductive communication, etc.), and communication between the MD 200 and the LCP 100 is performed via a conducted mode (e.g. conducted communication). In some examples, communication between the LCP 100 and the external support device 260 is accomplished by sending communication information through the MD 200. However, in other examples, communication between the LCP 100 and the external support device 260 may be direct. In some embodiments, the external support device 260 may be provided with or be in communication with a display 262. The display 262 may be a personal computer, tablet computer, smart phone, laptop computer, or other display as desired. In some instances, the display 262 may include input means for receiving an input from a user. For example, the display 262 may also include a keyboard, mouse, actuatable buttons, or be a touchscreen display. These are just examples.

Figure 4:
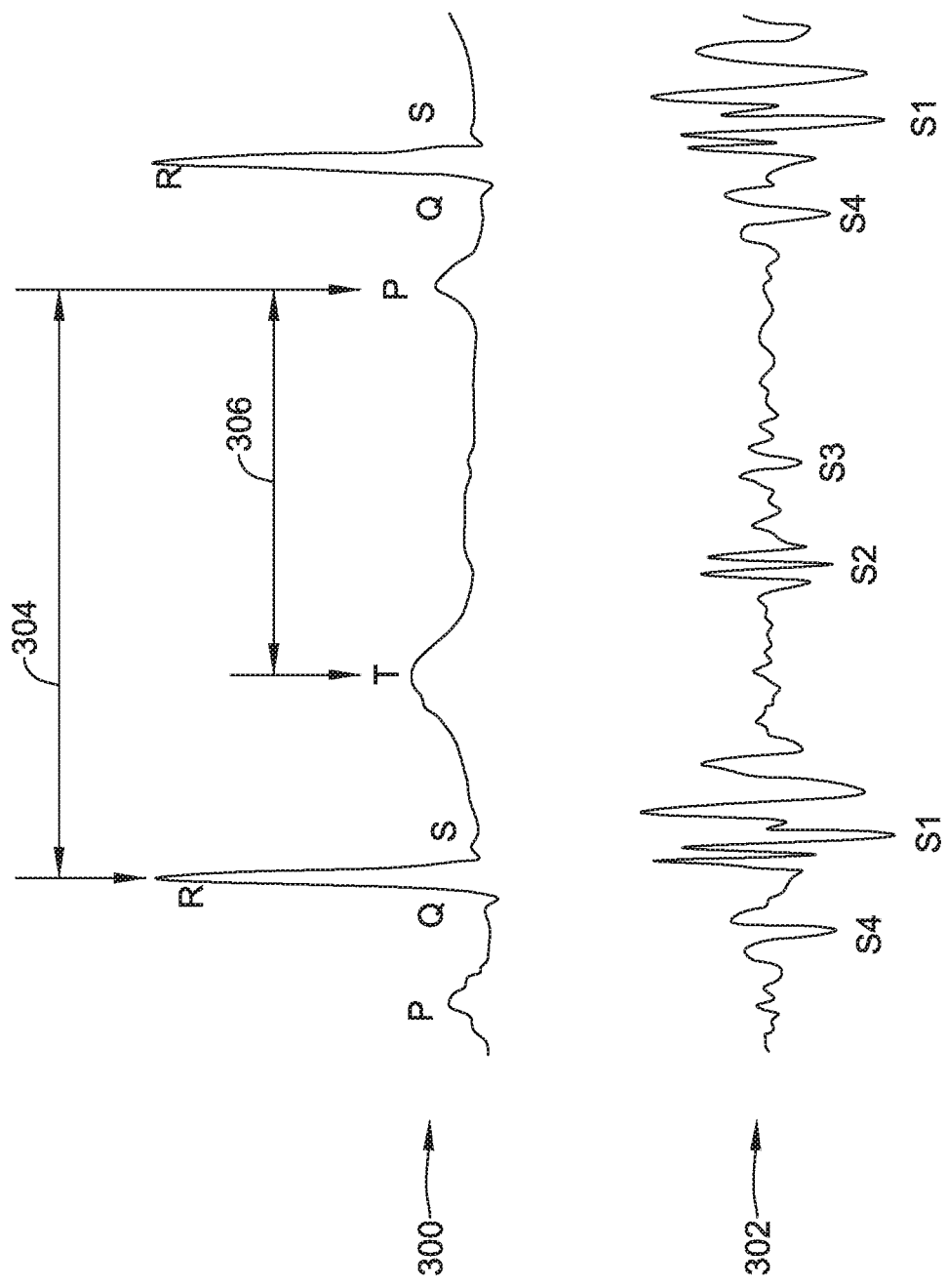
FIG. 4 is a graphical representation of an illustrative electrocardiogram (ECG) showing a temporal relationship between electrical signals of the heart and mechanical indications of contraction of the heart.

With reference to FIG. 4, it will be appreciated that the heart is controlled via electrical signals that pass through the cardiac tissue and that can be detected by implanted devices such as but not limited to the LCP 100 and/or MD 200 of FIG. 1 or 2. FIG. 4 is a graphical representation of an illustrative electrocardiogram (ECG) 300 showing a temporal relationship between electrical signals of the heart and mechanical indications 302 (e.g. heart sounds) of contraction of the heart. As can be seen in the illustrative ECG 300, a heartbeat includes a P-wave that indicates atrial depolarization associated with an atrial contraction to load the ventricles. A QRS complex, including a Q-wave, an R-wave and an S-wave, represents a ventricular depolarization associated with the ventricles contracting to pump blood to the body and lungs. A T-wave shows the repolarization of the ventricles in preparation for a next heart beat. With heart disease, the timing of these individual events may be anomalous or abnormal, and the shape, amplitude and/or timing of the various waves can be different from that shown. It will be appreciated that the ECG 300 may be detected by implanted devices such as but not limited to the LCP 100 and/or MD 200 of FIG. 1 or 2.

The electrical signal 300 typically instructs a portion of the heart to contract, which then results in a corresponding mechanical contraction. There is a correspondence between a characteristic in the electrical signal (e.g. ECG 300) and a corresponding mechanical response. The mechanical response is typically delayed because it takes some time for the heart to respond to the electrical signal.

It will be appreciated that heart sounds may be considered as one example of mechanical indications of the heart beating. Other illustrative mechanical indications may include, for example, endocardial acceleration or movement of a heart wall detected by an accelerometer in the LCP, acceleration or movement of a heart wall detected by an accelerometer in the SICD, a pressure, pressure change, or pressure change rate in a chamber of the heart detected by a pressure sensor of the LCP, acoustic signals caused by heart movements detected by an acoustic sensor (e.g. accelerometer, microphone, etc.), twisting of the heart detected by a gyroscope in the LCP and/or any other suitable indication of a heart chamber beating.

In some cases, there may be a first heart sound denoted 51 that is produced by vibrations generated by closure of the mitral and tricuspid valves during a ventricular contraction, a second heart sound denoted S2 that is produced by closure of the aortic and pulmonary valves, a third heart sound denoted S3 that is an early diastolic sound caused by the rapid entry of blood from the right atrium into the right ventricle and from the left atrium into the left ventricle, and a fourth heart sound denoted S4 that is a late diastolic sound corresponding to late ventricular filling during an active atrial contraction. These are mechanical responses that can be detected using various sensors (e.g. microphone, hydrophone, accelerometer, etc.).

Because the heart sounds are a result of cardiac muscle contracting or relaxing in response to an electrical signal, it will be appreciated that there is a delay between the electrical signal, indicated by the ECG 300, and the corresponding mechanical indication, indicated in the example shown by the heart sounds trace 302. For example, the P-wave of the ECG 300 is an electrical signal triggering an atrial contraction. The S4 heart sound is the mechanical signal caused by the atrial contraction. In some cases, it may be possible to use this relationship between the P-wave and the S4 heart sound. For example, if one of these signals can be detected, their expected timing relationship can be used as a mechanism to search for the other. For example, if the P-wave can be detected, a window following the P-wave can be defined and searched in order to help find and/or isolate the corresponding S4 heart sound. In some cases, detection of both signals may be an indication of an increased confidence level in a detected atrial contraction. In some cases, detection of either signal may be sufficient to identify an atrial contraction. The identification of an atrial contraction may be used to identify an atrial contraction timing fiducial (e.g. a timing marker of the atrial contraction).

With traditional systems having transvenous leads, the intracardiac electrodes are placed to detect the atrial depolarization while also delivering pacing therapy to one or both ventricles. As a result, the circuitry of a single device would receive, directly, information for the P-wave allowing delivery at a timed interval of a pacing pulse to properly coordinate the ventricular pace with the atrial contraction and improve pumping efficiency. However, with a system only having an LCP implanted within a ventricle, it may be difficult to detect the relatively small P-wave from within the ventricle, and as such, it is contemplated that the LCP may be configured to detect atrial activity without relying on the P-wave (e.g. using S4). The detected atrial activity may be used to identify an atrial timing fiducial that can be used as a basis for timing a pacing pulse in the ventricle (e.g. after an AV delay).

In some examples, a time window for atrial artifact detection is defined during which the LCP 100 may specifically look for atrial artifacts (such as, but not limited to, atrial contraction) to determine an atrial timing fiducial. Such windows may be defined by analysis of the cardiac signals obtained from a patient using, for example, a detected ventricular event such as the R-wave/QRS complex or the T-wave of a previous heart beat as the starting point for timing delays 304, 306, as shown in FIG. 4. Timing delays 304, 306 may be dynamic based on the overall heart beat rate of the patient using data gathered from a patient or using a formula or accepted relationship. Other windows may be determined based on detected atrial artifacts and/or determined atrial events, as described in more detail herein.

In some cases, the relationship of certain electrical signals and/or mechanical indications may be used to predict the timing of other electrical signals and/or mechanical indications within the same heartbeat. Alternatively, or in addition, the timing of certain electrical signals and/or mechanical indications corresponding to a particular heartbeat may be used to predict the timing of other electrical signals and/or mechanical indications within a subsequent heartbeat.

Figure 5:
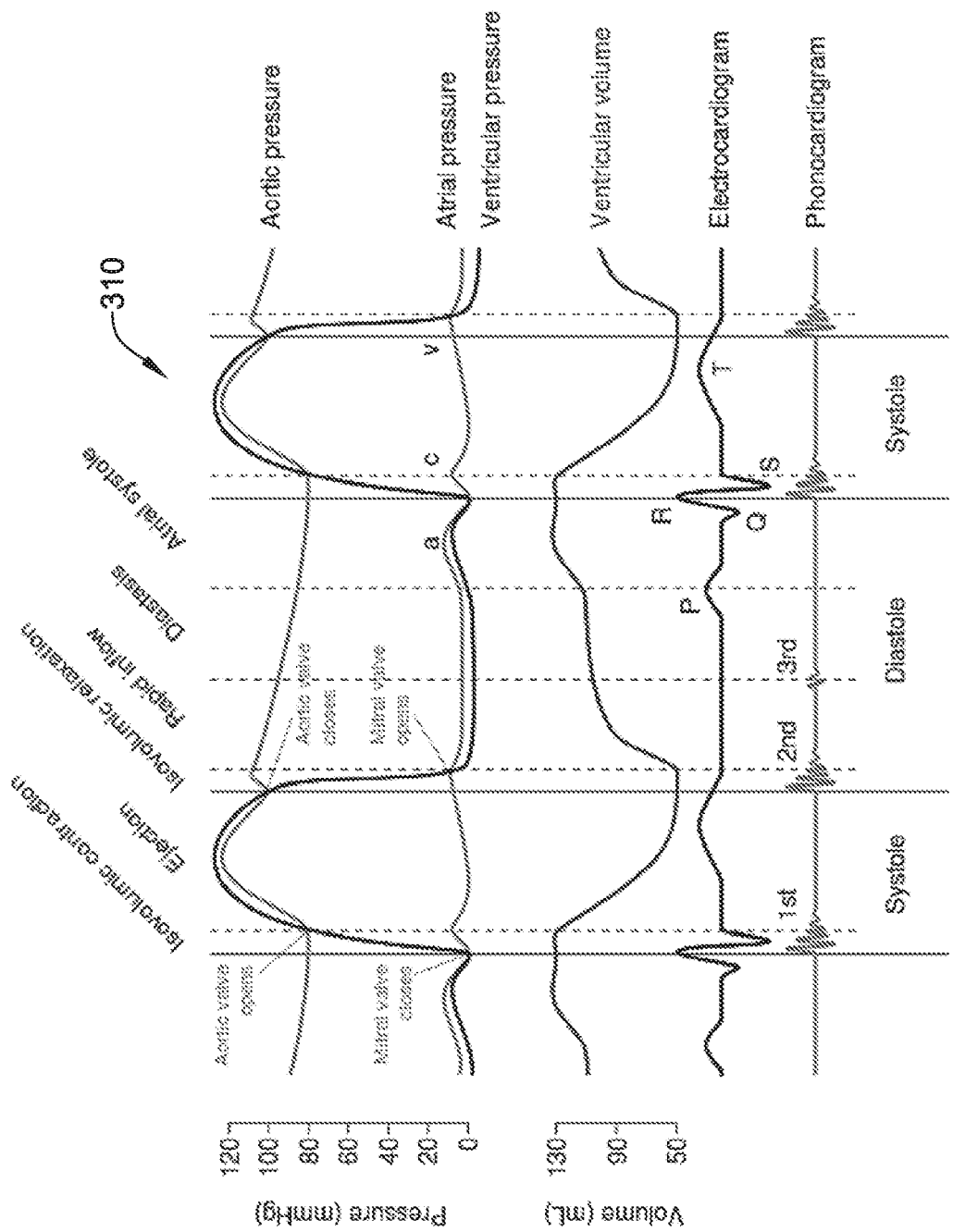
FIG. 5 is a graph showing example pressures and volumes within the heart over time.

It will be appreciated that as the heart undergoes a cardiac cycle, the blood pressures and blood volumes within the heart vary over time. FIG. 5 illustrates how these parameters correlate with the electrical signals and corresponding mechanical indications. FIG. 5 shows an illustrative example of the aortic pressure, left ventricular pressure, left atrial pressure, left ventricular volume, an electrocardiogram (ECG or egram), and heart sounds of the heart over two consecutive heart beats. A cardiac cycle may begin with diastole, and the mitral valve opens. The ventricular pressure falls below the atrial pressure, resulting in the ventricle filling with blood. During ventricular filling, the aortic pressure slowly decreases as shown. During systole, the ventricle contracts. When ventricular pressure exceeds the atrial pressure, the mitral valve closes, generating the S1 heart sound. Before the aortic valve opens, an isovolumetric contraction phase occurs where the ventricle pressure rapidly increases but the ventricle volume does not significantly change. Once the ventricular pressure equals the aortic pressure, the aortic valve opens and the ejection phase begins where blood is ejected from the left ventricle into the aorta. The ejection phase continues until the ventricular pressure falls below the aortic pressure, at which point the aortic valve closes, generating the S2 heart sound. At this point, the isovolumetric relaxation phase begins and ventricular pressure falls rapidly until it is exceeded by the atrial pressure, at which point the mitral valve opens and the cycle repeats.

Contractions of the atria are initiated near the end of ventricular diastole. The active atrial contraction pushes or forces additional volumes of blood into the ventricles (often referred to as "atrial kick") in addition to the volumes associated with passive filling. In some cases, the atrial kick contributes in the range of about 20% of the volume of blood toward ventricular preload. At normal heart rates, the atrial contractions are considered highly desirable for adequate ventricular filling. However, as heart rates increase, atrial filling becomes increasingly important for ventricular filling because the time interval between contractions for active filling becomes progressively shorter. Cardiac pressure curves for the pulmonary artery, the right atrium, and the right ventricle, and the cardiac volume curve for the right ventricle, may be similar to those illustrated in FIG. 5. Typically, the cardiac pressure in the right ventricle is lower than the cardiac pressure in the left ventricle.

The heart sound signals shown in FIG. 5 can be recorded using acoustic sensors, for example a microphone, which may capture the acoustic waves resulted from such heart sounds. In another example, the heart sounds can be recorded using accelerometers or pressure sensors that capture the vibrations or pressure waves caused by the heart sounds. The heart sound signals can be recorded within or outside the heart. These are just examples.

In some cases, sensing atrial events or artifacts indicative of an atrial event may allow a device, such as LCP 100 implanted in the ventricle, to detect an atrial contraction, resulting in, for example, an atrial kick. In some cases, signals that provide an indication of an atrial contraction may include one or more of an S3 heart sound signal, an S4 heart sound signal, an A-wave signal (pressure wave) and a P-wave signal. In some cases, signals that can provide an indication of a ventricular contraction may include one or more of an R-wave, a ventricle pressure signal, a ventricle change in pressure signal (dP/dt), a ventricle wall acceleration signal, a ventricle twist signal, a blood flow rate signal, and a ventricle volume signal. These are just some examples.

Some other events or artifacts detected may include, but are not limited to, S1 heart sounds, S2 heart sounds, ventricular volume, ventricular wall dimension, cardiac tissue and/or blood vibration, atrium to ventricle blood movement, ventricular wall and/or atrioventricular (AV) valve position, akinetic pressure, ventricular twist, and any other event or artifact suitable for identifying an atrial event, and/or combinations thereof.

It is contemplated that a number of different sensor modalities may be used to help detect atrial events or artifacts indicative of an atrial event from the ventricle. FIG. 6 shows a table 320 that includes a column for each of various illustrative artifact(s), and a row for each illustrative sensor modality. An "X" indicates the sensor modalities that may be used to detect the corresponding artifact.

In FIG. 6, it can be seen that voltage may be used to detect P-waves, such as via an electrogram or an electrocardiogram (ECG). It is contemplated that, in some cases, an LCP implanted in the right ventricle may have a free end (e.g. end that is not affixed to the tissue) pointed towards the tricuspid valve. Due to their anatomical proximity, the electrodes of the LCP may be used to detect atrial depolarization (e.g., the p-wave). From the ventricle, the p-wave may be relatively small and difficult to detect. In some cases, the LCP may identify a time window around when the p-wave is expected, and the LCP may increase amplification and/or add special filtering and/or signal averaging (e.g. see FIG. 11) to help identify the p-wave during the window. Alternatively, or in addition, the p-wave may be detected along with one or more other artifacts to help confirm an atrial contraction and to develop an atrial timing fiducial therefrom.

As shown in FIG. 6, pressure may be used to identify a number of different atrial artifacts. For example DC and/or near DC type pressure measurements (e.g. 0-10 Hz range) may be used to identify passive filling of the ventricle (e.g., akinetic pressure). Low frequency (e.g. 1-5 Hz range) AC type pressure measurements may be used to detect the A-wave (atrial pressure wave in the ventricle), while higher frequency (e.g. 15-30 Hz range) AC type pressure measurements may be used to detect heart sounds. These are just examples. In some cases, pressure may be used to identify the transition between passive and active filling modes. This transition may be used as an indicator of atrial contraction. Other suitable methods for measuring or detecting pressure in one or more heart chambers may also be used, as desired. Some illustrative but non-limiting pressure sensors and configurations for sensing pressure using an LCP are described in commonly assigned Patent Application No. 62/413,766 entitled "IMPLANTABLE MEDICAL DEVICE WITH PRESSURE SENSOR and filed on Oct. 27, 2016, and Patent Application No. 62/547,458, entitled IMPLANTABLE MEDICAL DEVICE WITH PRESSURE SENSOR and filed on Aug. 18, 2017, which are hereby incorporated by reference.

As shown in FIG. 6, impedance measurements may be used to determine ventricular volume changes which may then be used to infer a pressure wave (e.g. A-wave) due to an atrial contraction. In one example, as the volume of blood in the ventricle changes, the impedance between the electrodes of the LCP changes. It is contemplated that the rate of change in the volume (e.g., an increase in the rate of blood entering the ventricle and hence a faster change in volume of the ventricle) may be used to identify the start of active filling and thus an atrial contraction. Some illustrative uses of impedance measurements in the heart are described in commonly assigned patent application Ser. No. 15/630,677 entitled LEADLESS CARDIAC PACEMAKER FOR GENERATING CARDIAC PRESSURE-VOLUME LOOP and filed on Jun. 22, 2017, which is hereby incorporated by reference.

As blood enters the ventricle as a result of an atrial contraction, the ventricle may stretch. The stretching of the ventricle may be measure with a strain sensor. A strain sensor may require two or more points of fixation. Acceleration may be used to measure contractility of the heart H, as well as sounds. In some cases, cardiac output can be determined when acceleration measurements are combined with ventricle pressure, cardiac volume and/or other sensed parameters.

It should be understood that the table 320 shown in FIG. 6 is not intended to include every possible artifact or sensor modality for detecting each artifact. Those of skill in the art will recognize that other artifacts, sensor modalities and/or combinations thereof may be used to identify an atrial event from the ventricle. In one additional example, a respiratory phase sensor may be used with other atrial artifacts described herein or by itself to help identify an atrial artifact.

The atrial event and/or artifacts indicative of an atrial event may occur during either or both passive ventricular filling or active ventricular filling. FIG. 7 illustrates a table 330 of the cardiac phases, and the artifact(s) that may occur during that phases of the cardiac cycle, where an "X" is used to denote that the corresponding artifact occurs during the identified cardiac phase. Due to an electromechanical delay, the initial portion of the P-wave may fall into the passive filling phase while the later portion may fall into the active filling phase, and that is why an "X" is in both rows of the table 330. Although not required, it is contemplated that force per unit area type measurements may be provided as a DC voltage or current and/or a low frequency pressure signal linearly proportional to pressure. Sound type pressure measurements (e.g., infrasonic and sonic) may be provided as an AC pressure.

In some instances, ultrasound may use a combined ultrasound source and sensor, although this is not required. The source and sensor may be separately provided, as desired. It is contemplated that ultrasound imaging may be used in a device implanted in the ventricle to see the atrial wall (e.g., through the tricuspid valve), tricuspid closing, and/or a flow increase due to an atrial contraction to help identify an A-wave. In some cases, ultrasound sensor may detect an atrial arrhythmia (e.g. atrial flutter or atrial fibrillation). During normal sinus rhythm (NSR) atrial blood flow into the ventricle is comprised of two sequential components, an E (early) wave followed by an A (atrial) wave. During atrial arrhythmias the E wave is largely unchanged from that in NSR, however the A wave is either missing (atrial fibrillation) or smaller and much faster (atrial flutter). During a detected atrial arrhythmia an LCP with an ultrasound sensor may modify its behavior (e.g. revert from VVD mode to VVI mode).

It should be noted that while the heart sounds are indicated as capable of being identified with an accelerometer, the accelerometer actually measures or detects mechanical vibration associated with the heart sound and not the pressure of the sound waves. In some cases, the measured artifact may not occur distinctly within one cardiac phase or another. For example, ventricular twist may be used to identify the end of active ventricular filling (e.g., ejection). Further, the S1 heart sound may occur at the end of active ventricular filling, while the S2 heart sound may occur shortly before the beginning of passive ventricular filling. These are just some examples.

In some cases, the LCP 100 may be configured to determine an atrial contraction timing fiducial based at least in part upon a sensed indication of an atrial contraction in a first heartbeat and/or a sensed indication of a ventricular contraction in the first heartbeat and/or one or more immediately preceding heartbeat(s). In some cases, the processing module 110 of the LCP 100 may be configured to generate and deliver a ventricle pacing pulse using the determined atrial contraction timing fiducial (e.g. after an A-V delay).

As described above, atrial events or artifacts indicative of an atrial event may be used by an LCP in the ventricle (e.g. right ventricle) to time a pacing pulse for the ventricle in support of treating bradycardia events. In some cases, the timing of the ventricle pacing pulse may be adjusted to improve the amount of blood entering the right ventricle through active filling. In some instances, this may include adjusting an AV delay relative to an atrial fiducial (e.g., atrial kick). In some cases, a measured pressure change (or other atrial fiducial) over time may be used to support management of a CRT cardiac therapy (if placed in the left ventricle), patient health status monitoring and/or any other suitable goal. It is contemplated that detecting events in one of or both of the ventricle and atrium using a single LCP implanted in the ventricle may replicate a dual chamber system with only a single device. That is, a single device positioned in the ventricle may listening to both the ventricle and the atrium and pacing accordingly (e.g., a VDD device).

FIG. 8 is a side view of an illustrative implantable leadless cardiac pacemaker (LCP) 400 which may be positioned within the ventricle and configured to listen to both the ventricle and the atrium. The LCP 400 may be similar in form and function to the LCP 100 described above. The LCP 400 may include any of the sensing, electrical, control, and/or pacing modules and/or structural features described herein. The LCP 400 may include a shell or housing 402 having a proximal end 404 and a distal end 406. The illustrative LCP 400 includes a first electrode 410 secured relative to the housing 402 and positioned adjacent to the distal end 406 of the housing 402 and a second electrode 412 secured relative to the housing 402 and positioned adjacent to the proximal end 404 of the housing 402. In some cases, the housing 402 may include a conductive material and may be insulated along a portion of its length. A section along the proximal end 404 may be free of insulation so as to define the second electrode 412. The electrodes 410, 412 may be sensing and/or pacing electrodes to provide electro-therapy and/or sensing capabilities. The first electrode 410 may be capable of being positioned against or otherwise in contact with the cardiac tissue of the heart, while the second electrode 412 may be spaced away from the first electrode 410. The first and/or second electrodes 410, 412 may be exposed to the environment outside the housing 402 (e.g., to blood and/or tissue).

It is contemplated that the housing 402 may take a variety of different shapes. For example, in some cases, the housing 402 may have a generally cylindrical shape. In other cases, the housing 402 may have a half-dome shape. In yet other embodiments, the housing 402 may be a rectangular prism. It is contemplated that the housing may take any cross sectional shape desired, including but not limited to annular, polygonal, oblong, square, etc.

In some cases, the LCP 400 may include a pulse generator (e.g., electrical circuitry) and a power source (e.g., a battery) within the housing 402 to provide electrical signals to the electrodes 410, 412 to control the pacing/sensing electrodes 410, 412. While not explicitly shown, the LCP 400 may also include a communications module, an electrical sensing module, a mechanical sensing module, and/or a processing module, and the associated circuitry, similar in form and function to the modules 102, 106, 108, 110 described above. The various modules and electrical circuitry may be disposed within the housing 402. Electrical communication between the pulse generator and the electrodes 410, 412 may provide electrical stimulation to heart tissue and/or sense a physiological condition.

In the example shown, the LCP 400 includes a fixation mechanism 414 proximate the distal end 406 of the housing 402. The fixation mechanism 414 is configured to attach the LCP 400 to a wall of the heart H, or otherwise anchor the LCP 400 to the anatomy of the patient. As shown in FIG. 8, in some instances, the fixation mechanism 414 may include one or more, or a plurality of hooks or tines 416 anchored into the cardiac tissue of the heart H to attach the LCP 400 to a tissue wall. In other instances, the fixation mechanism 414 may include one or more, or a plurality of passive tines, configured to entangle with trabeculae within the chamber of the heart H and/or a helical fixation anchor configured to be screwed into a tissue wall to anchor the LCP 400 to the heart H. These are just examples.

The LCP 400 may further include a docking member 420 proximate the proximal end 404 of the housing 402. The docking member 420 may be configured to facilitate delivery and/or retrieval of the LCP 400. For example, the docking member 420 may extend from the proximal end 404 of the housing 402 along a longitudinal axis of the housing 402. The docking member 420 may include a head portion 422 and a neck portion 424 extending between the housing 402 and the head portion 422. The head portion 422 may be an enlarged portion relative to the neck portion 424. For example, the head portion 422 may have a radial dimension from the longitudinal axis of the LCP 400 that is greater than a radial dimension of the neck portion 424 from the longitudinal axis of the LCP 400. In some cases, the docking member 420 may further include a tether retention structure 426 extending from or recessed within the head portion 422. The tether retention structure may define an opening 428 configured to receive a tether or other anchoring mechanism therethrough. The retention structure may take any shape that provides an enclosed perimeter surrounding the opening such that a tether may be securably and releasably passed (e.g., looped) through the opening 428. In some cases, the retention structure may extend though the head portion 422, along the neck portion 424, and to or into the proximal end 404 of the housing 402. The docking member 420 may be configured to facilitate delivery of the LCP 400 to the intracardiac site and/or retrieval of the LCP 400 from the intracardiac site. While this describes one example docking member 420, it is contemplated that the docking member 420, when provided, can have any suitable configuration.

It is contemplated that the LCP 400 may include one or more sensors 430 coupled to or formed within the housing 402 such that the sensor(s) is exposed to and/or otherwise operationally coupled with (e.g., responsive to) the environment outside the housing 402 to measure or detect various artifacts within the heart. The one or more sensors 430 may be of a same modality or a combination of two or more different sensing modalities, as desired. For example, the one or more sensors 430 may be use voltage, pressure, sound, ultrasound, impedance, strain, acceleration, flow, and/or rotation to detect P-waves, A-waves, S1-S4 heart sounds, ventricular volume, ventricular wall dimensions, cardiac tissue and/or blood vibration, atrium to ventricle blood movement, ventricular wall and/or atrioventricular valve position, akinetic pressure, and/or ventricular twist, such as described with respect to FIGS. 6 and 7. The sensors may be a part of, coupled to, and/or in electrical communication with a sensing module disposed within the housing 402. In addition to sensing artifacts within the heart, the sensing module may be further configured to detect physiological conditions that may impact the LCP's ability to detect artifacts including, but not limited to posture, activity and/or respiration. The use of two or more sensors in combination may allow for the removal of some common mode noise (e.g., may eliminate gross body motion).

In some cases, the one or more sensors 430 may be coupled to an exterior surface of the housing 402. In other cases, the one or more sensors 430 may be positioned within the housing 402 with an artifact acting on the housing and/or a port on the housing 402 to affect the sensor 430. In one illustrative example, if the LCP 400 is placed in the right ventricle, the sensor(s) 430 may be a pressure sensor configured to measure a pressure within the right ventricle. If the LCP 400 is placed in another portion of the heart (such as one of the atriums or the left ventricle), the pressures sensor(s) may measure the pressure within that portion of the heart. In some cases, the sensor(s) 430 may be sensitive enough to detect an artifact in a heart chamber different from the chamber in which the LCP 400 is positioned. For example, in some instances a sensor 430 may detect a pressure change caused by an atrial contraction (e.g., atrial kick) when the LCP 400 is placed in the right ventricle. Some illustrative sensor configurations will be described in more detail herein.

Figure 9A:
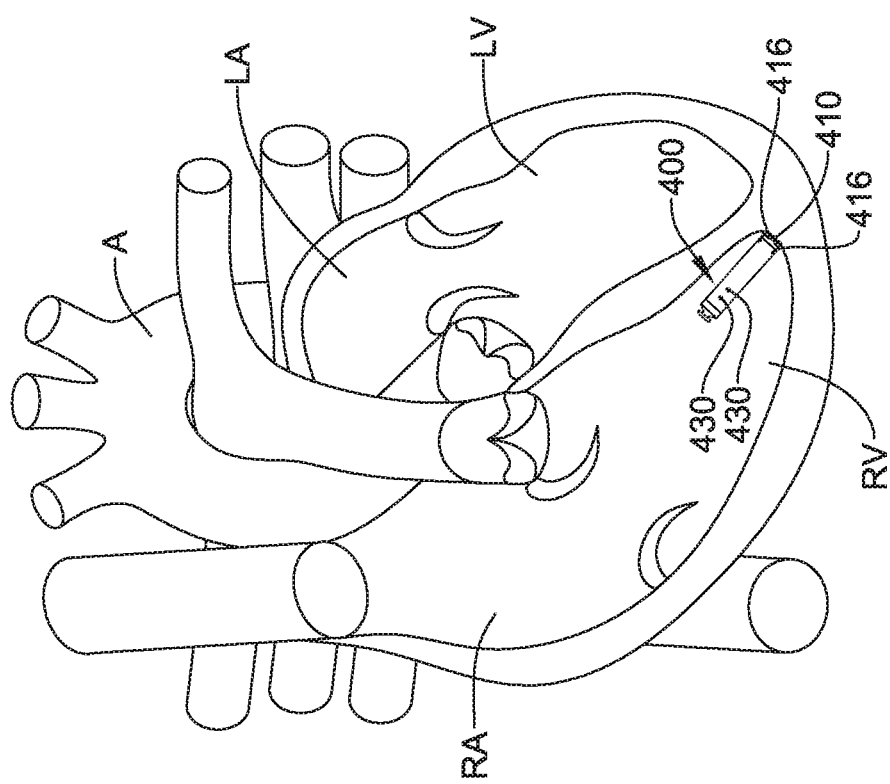
FIG. 9A is a partial cross-sectional plan view of an example LCP implanted within a heart during ventricular filling.
Figure 9B:
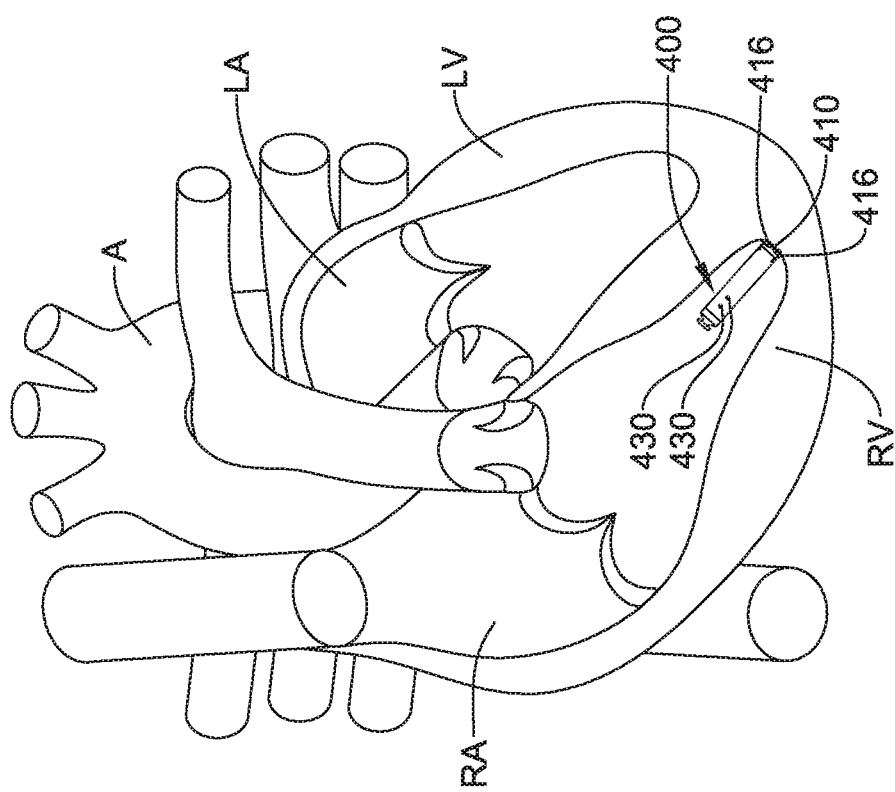
FIG. 9B is a partial cross-sectional plan view of an example LCP implanted within a heart during ventricular contraction.

FIG. 9A is a plan view of the example leadless cardiac pacing device 400 implanted within a right ventricle RV of the heart H during ventricular filling. The right atrium RA, left ventricle LV, left atrium LA, and aorta A are also illustrated. FIG. 9B is a plan view of the leadless cardiac pacing device 610 implanted within a right ventricle of the heart H during ventricular contraction. These figures illustrate how the volume of the right ventricle may change over a cardiac cycle. As can be seen in FIGS. 9A and 9B, the volume of the right ventricle during ventricular filling is larger than the volume of the right ventricle of the heart after ventricular contraction.

While it is desirable to identify an atrial contraction often associated with the A-wave, the A-wave can be difficult to detect as it may be very small in magnitude and detection of it may come and go. It is contemplated that a combination of sensor modalities and/or measured atrial artifacts may be used to identify an atrial timing fiducial. For example, it is contemplated that any of the sensor modalities identified with respect to FIGS. 6 and 7 may be combined with any other sensor modality to identify an atrial timing fiducial. In some cases, a pressure signal may be used to determine a number of parameters. For example, a pressure signal may be used to determine or detect an A-wave (atrial kick). In another example, the pressure signal may be used to determine or detect a pressure pulse or pressure vibrations associated with S4, which may, for example, be in the 15-30 Hz range. In some cases, the S4 heart sound may be easier to detect using a pressure signal from a pressure sensor than from an accelerometer signal from accelerometer or using an acoustic signal from an acoustic sensor, particularly since the ventricular pressure is not changing substantially during this time period (ventricle is filling) and since there may be a great deal of unwanted signal (i.e. noise) in the accelerometer signal due to patient activity. In another example, a pressure signal may be used to determine a change in ventricle pressure relative to time (dP/dt).

In some cases, the circuitry and/or processing module of the LCP 400 may also be configured determine an atrial contraction timing fiducial based at least in part upon two or more of a signal received from the electrical sensing module, mechanical sensing module, and/or communication module. In some cases, the electrical cardiac signal received via the electrode arrangement 410, 412 may include at least a portion of an electrocardiogram (ECG). In some cases, the electrical cardiac signal received via electrode arrangement 410, 412 may include a P-wave. In some instances, the electrical cardiac signal received via the electrode arrangement 410, 412 may include a QRS complex, from which a QRS width can be determined. In some cases, the electrical cardiac signal received via electrode arrangement 410, 412 may include two consecutive R waves, from which an R-wave to R-wave interval can be determined. In some cases, the electrical cardiac signal may include a conducted or other communicated electrical signal from another device (e.g. SICD device) that includes an indication of an atrial or other contraction of the heart H. In some cases, the processing module and/or circuity may be configured to generate and deliver a ventricle pacing pulse using the atrial contraction timing fiducial.

It is contemplated that the use of sensors to determine an atrial contraction timing fiducial without having to detect the A-wave may allow the LCP 100, 400 to predict or recognize when an A-wave likely occurred, even when the A-wave itself was not detected. The predicted time of the A-wave may then be used as an atrial contraction timing fiducial for pacing the ventricle. The A-wave may be particularly difficult to detect when, for example, the heart is experiencing atrial fibrillation, a patient is in certain postures, the respiration rate is high, the patient activity is high, the heart rate is high, the atria are hypocontractile or akinetic, and/or during periods of high heart rate variability (HRV).

In the cardiac cycle, the ventricles receive blood from the atria first through passive filling and then through active filling. Discussion of passive and active filling will be described with reference to a right side of the heart, however, it should be understood that a similar process is occurring in the left side of the heart. Passive filling of the right ventricle begins when the there is a pressure gradient between the chambers causing the tricuspid valve to open and blood accumulated in the right atrium to flow into the right ventricle. Both the right atrium and the right ventricle continue to fill as blood returns to the heart. The right atrium contracts near the end of ventricular diastole. Atrial depolarization begins at the P-wave of the electrocardiogram. As a result of the P-wave, atrial cells develop tension and shortening causing the atrial pressure to increase (e.g. A-wave). These active contraction forces force additional volumes of blood into the ventricle (often referred to as the "atrial kick"). The active contraction forces begin the active filling phase. At normal heart rates, the atrial contractions are considered desirable for adequate ventricular filling. As heart rate increases, atrial filling becomes increasingly important for ventricular filling because the time interval between contractions for filling becomes progressively shorter. Atrial fibrillation and/or asynchronized atrial-ventricular contractions can result in a minimal contribution to preload via atrial contraction.

As described above, the fourth heart sound (e.g., S4) is typically a gallop sound that results from a forceful atrial contraction during presystole that ejected blood into a ventricle which cannot expand further. The fourth heart sound occurs during the last one-third of diastole about 90 milliseconds before S1. The frequency of S4 may be in the range of about 15 Hertz (Hz) to about 30 Hz, although the frequency may sometimes be outside this range. Due to the low pitch, S4 (and sometimes S3) are usually not audible with a typical stethoscope. It is contemplated that the S4 heart sound may be used to identify the start of active filling of the ventricle. In some cases, the processing module 110 and/or circuitry may be programmed to begin looking for the S4 heart sound just before the S1 heart sound is expected (projected from one or more previous heart beats).

The heart sounds may be time dependent on the heart rate in manner that changes linearly with the heart rate. For example, as the heart rate increases, the time between the heart sounds (e.g. S1 to S1; S4 to S1, etc.) may decrease in a linear and predicable manner. This may allow the S4 heart sound to be used to identify a reliable atrial event and/or as an atrial timing fiducial over a range of heart rates.

As noted above, the S4 heart sound may be identified and/or detected using a variety of different sensors, including but not limited to a higher frequency pressure sensor (e.g. 15 to 30 Hz), a hydrophone, a microphone, and/or an accelerometer. These are just some examples of how the LCP 400 can detect an artifact during active ventricular filling and identify an atrial timing fiducial based on the detected artifact.

While the above example was described with respect to active filling, it is contemplated that an artifact identified during passive filling may also be used to identify an atrial event which may then be used to identify an atrial timing fiducial. For example, the third heart sound (e.g., S3) occurs near the middle of passive filling. Passive filling may generate a very low frequency sound (in the range of 0 to 10 Hz) which may be detected by a DC capable pressure sensor. This may allow the S3 heart sound to be used to identify an atrial event and/or as an atrial timing fiducial over a range of heart rates.

Figure 10:
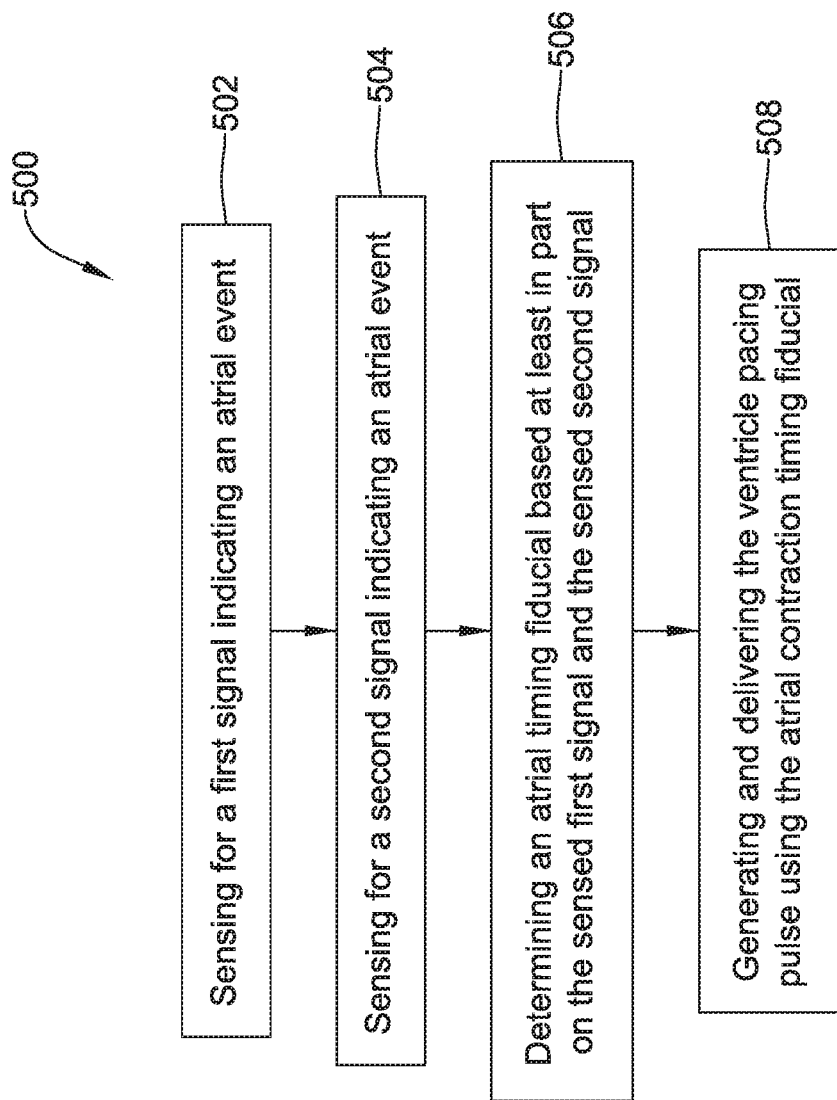
FIG. 10 is a flow diagram showing an illustrative method of detecting atrial activity from an LCP implanted in a ventricle of the heart and generating and delivering a ventricular pacing pulse using the same.

FIG. 10 is a flow diagram showing an illustrative method 500 of generating a ventricular pulse using an LCP that is disposed with the right ventricle. In some cases, as indicated at block 502, a first signal (e.g., an atrial artifact) indicating an atrial event of a patient's heart may be sensed with a sensing module of the LCP. A second different signal related to the atrial event of the patient's heart may also be detected, as indicated at block 504. The second different signal may be sensed by the LCP, or may be received from another device (e.g. an SICD or another LCP) via a communication module of the LCP.

In some instances, the first signal and/or the second signal may be generated via one or more sensors within or on the housing the LCP. As described above, the sensing module of the LCP 400 may sense different events depending on whether attempting to identify active filling or passive filling (see FIG. 7). Some illustrative sensing modalities for sensing active filling may include, but are not limited to impedance, strain, sound, rotation, or flow, any or all of which may be used to detect at least one of a P-wave, S2 heart sound, S3 heart sound, ventricular volume, ventricular wall dimension, ventricular blood movement, ventricular wall movement, tricuspid valve position, mitral valve position, and/or akinetic ventricular pressure. Some illustrative sensing modalities for sensing passive filling may include, but are not limited to pressure, impedance, strain, sound, rotation, acceleration, voltage, and flow, which may be used to detect at least one of a P-wave, A-wave, S1 heart sound, S4 heart sound, ventricular volume, ventricular wall dimension, cardiac tissue vibration, ventricular blood movement, ventricular wall movement, tricuspid valve position, and mitral valve position.

The circuitry within the LCP 400 may be configured to determine an atrial timing fiducial based at least in part on the first and/or second sensed signals, as indicated at block 506. For example, the circuitry may be configured to determine when the A-wave occurs based on a sensed S4 heart sound and/or other atrial artifact. This is just one example. Those skilled in the art will recognize that any number of artifacts (or combinations thereof) can be used to determine an atrial timing fiducial. The circuitry may be configured to then generate and deliver a ventricular pacing pulse using the determined atrial timing fiducial, as indicated at block 508. The control circuitry may delay delivering a pacing pulse to the ventricle until an appropriate AV delay expires after the determined atrial timing fiducial. Notably, a different AV delay may be used for different atrial timing fiducials (see FIG. 14).

While the control timing of the pacing pulse may be triggered by an atrial timing fiducial that is based on arterial artifacts detected during a single heart beat, it is contemplated that the pacing pulse may be triggered by an atrial timing fiducial that is based on arterial and/or other artifacts detected during two or more previous heart beats.

In some cases, the LCP may determine an average timing for a particular atrial artifact and/or atrial timing fiducial over multiple heart beats.

The circuitry of the LCP may further be configured to determine intrinsic intervals within the cardiac cycle. This capability may be provided within the control circuitry or provided as a separate interval determination module in the LCP. In some cases, the circuitry may be configured to identify intrinsic intervals including atrial to atrial event or artifact intervals, atrial to ventricle event or artifact intervals, ventricle to atrial event or artifact intervals, and/or ventricle to ventricle event or artifact intervals. This information may be useful in predicting when, for example, an atrial event (e.g. A-wave) is expected to occur. This may be useful in, for example, confirming an atrial event that is sensed by the LCP. This may also be useful in identifying a window of time around which an atrial event is expected, such that the LCP may increase amplification and/or add special filtering and/or signal averaging (e.g. see FIG. 11) to help identify the atrial event during the window.

In some cases, the sensing module of the LCP may be configured to manipulate the signal prior to identifying an atrial event. For example, the sensing module may include one or more filters for filtering a signal. In some cases, the filter may include a first filter for passing a first frequency band, a second filter for passing a second frequency band, and a third filter for passing a third frequency band. The filter may include more than three frequency bands or fewer than three frequency bands, as desired. In some cases, the filter may be band-pass filter, a low pass filter, a high pass filter, and/or any other suitable filter. In some cases, a band-pass filter may be in the range of 1 to 5 Hz. In other cases, a bandpass filter may be in the range of 15 to 30 Hz. In yet another example, the filter may be a low-pass filter in the range of 0 to 10 Hz. These are just examples; other frequency ranges can be used, as desired. Also, filters may be employed that are not based on frequency, but rather some other signal feature such as amplitude, phase, etc.

Figure 11:
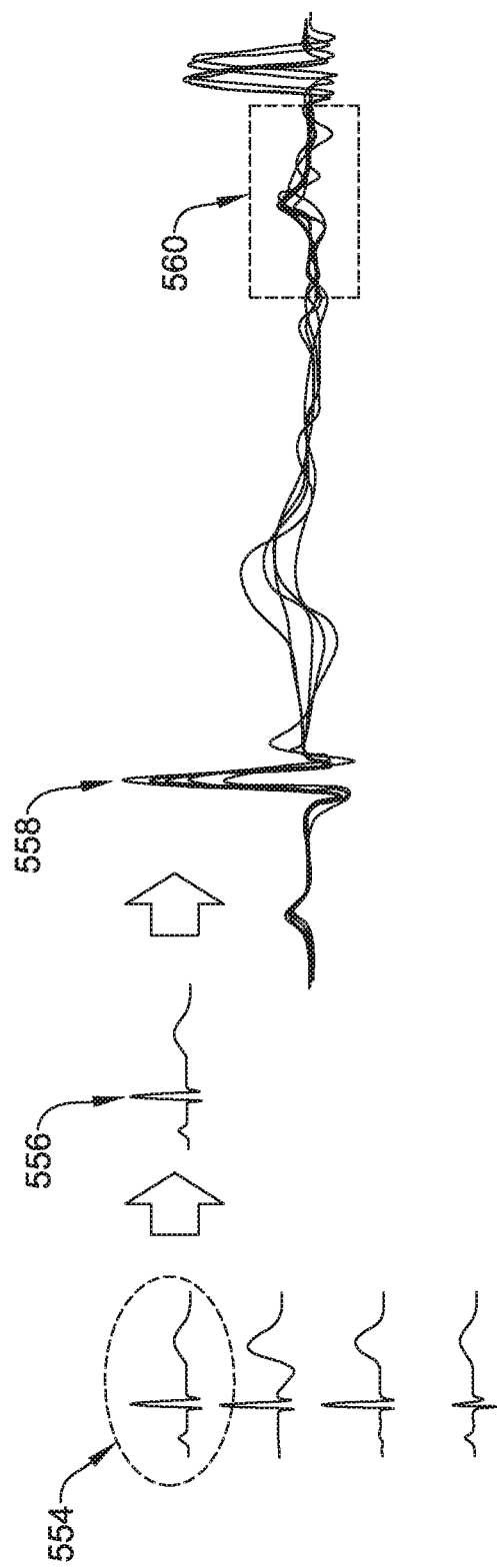
FIG. 11 is a schematic diagram of an illustrative signal averaging method that can be used by an LCP implanted in the ventricle to help identify atrial timing fiducials.

In some cases it may be desirable to limit the time frame in which the LCP 400 is looking for an atrial artifact. For example, battery life may be increased when the circuitry is searching for an artifact only during a limited window or period of time that is less than an entire cardiac cycle. The method for determining a time window for searching for an atrial artifact may include first identifying an expected time frame for the atrial event (e.g., atrial contraction) and then defining a search window accordingly. Referring to FIG. 11, to begin, the control module may select one or more signals with a desirable characteristic for a first timing fiducial signal to use as a time reference. The signal may be one or more of a pressure signal, an acoustic single, an acceleration signal, an electrical signal, etc. It is contemplated that the fiducial signal may be a different signal from the signal used to identify an atrial artifact and hence an atrial event or atrial timing fiducial. In the example shown in FIG. 12, the selected signal may be an ECG 554 generated from electrical signals in the right ventricle. Within the ECG 554, a specific feature, such as, but not limited to the R-wave may be selected as the fiducial reference feature 556. The ECGs 554 signals for a plurality of cardiac cycles (e.g., at least two or more) may be averaged, with the fiducial reference features 556 in each ECG 554 aligned. This signal averaging technique may help reveal small signals by canceling out random noise. The signal averaging technique may also be used to identify various cardiac events, atrial event templates, appropriate A-V delays for a variety of different atrial timing fiducials (e.g. A-wave, P-wave, R-wave, and/or other atrial timing fiducial).

A window 560 where an atrial event is expected to occur can then be isolated. For example, an atrial event (e.g., atrial contraction) may be expected to occur within a time window 560 before the next R-wave. Using this time window 560, the LCP may search for the atrial event. In some cases, the LCP may increase amplification and/or add special filtering and/or signal averaging to help identify the atrial event during the time window 560. In some case, the window 560 can be used as a reference point for determining another window in which another signal should be recorded and searched to identify an atrial artifact from which an atrial event can be deduced.

Figure 12:
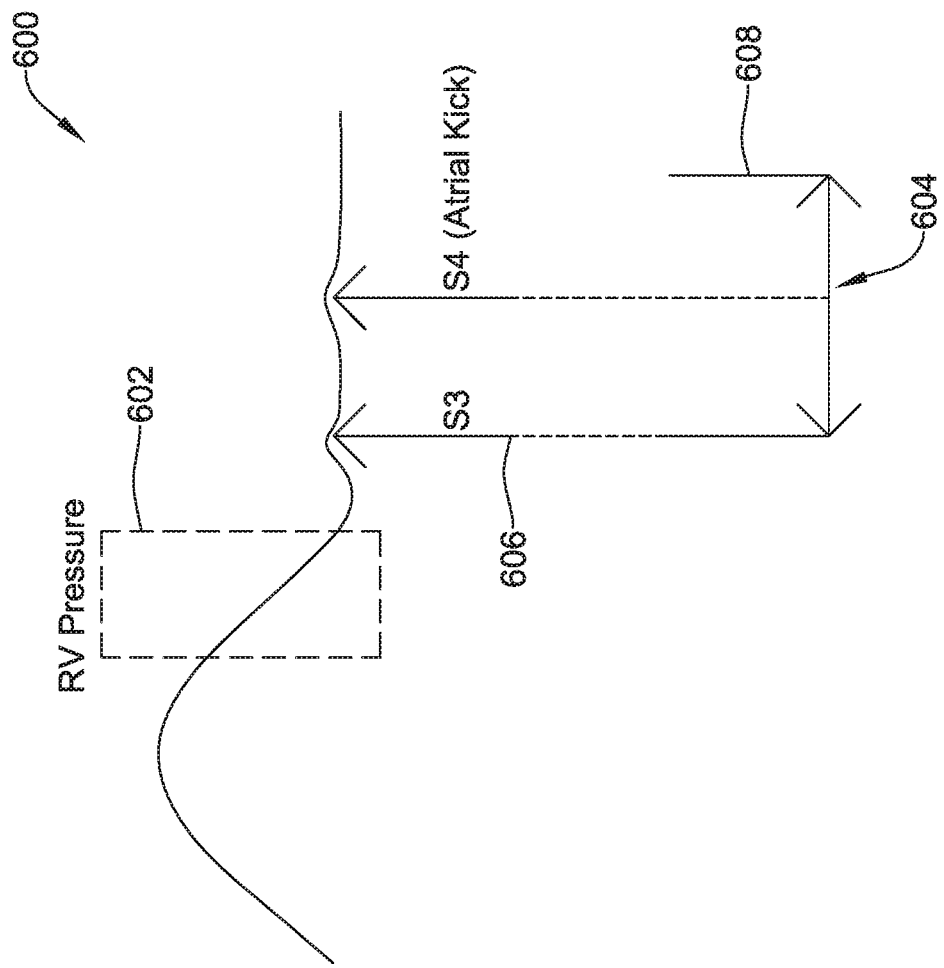
FIG. 12 shows a portion of an illustrative ventricle pressure signal.

In some cases, the timing window for identifying an atrial contraction may be based on artifacts occurring during passive filling of the ventricle. In some cases the downstroke of the ventricular pressure (e.g., when the A-V valve opens) may be used to open a timing window for detecting an atrial artifact and/or atrial contraction. An upslope in ventricular pressure may trigger an open sensing window to detect the atrial kick. FIG. 12 illustrates a portion of the pressure profile 600 of the right ventricle relative to the S3 and S4 heart sounds. The right ventricle may have an increase in pressure at the start of systole. The pressure may decrease as blood exits the ventricle. This sharp decrease in pressure may signal the control module to open a search window. For example, the search window may be opened in the general time frame indicated by box 602. This may command the control module to begin searching for an atrial artifact that may be used to start a timing window. The timing window 604 may open at the S3 heart sound 606 and close at the R-wave 608. The S4 heart sound and the atrial kick may occur within this timing window, as shown. It is contemplated that the control module may utilize automatic gain control to increase the sensitivity (e.g., reduce the threshold and/or increase the gain) over the period of the timing window to help increase the sensitivity when the expected event (e.g., atrial kick) is expected to occur.

In another example, the S2 heart sound may be used to identify the start of passive filling. It is contemplated that a pressure sensor in the LCP may be used to detect the pressure change associated with the atrial kick, or any of the atrial artifacts identified herein can be used either alone or in combination with the atrial kick as the atrial timing fiducial. The LCP 100, 400 can then pace the ventricle based off of the artifact, the atrial kick or a combination thereof. In another example, ventricular impedance may be used to identify volume changes in the ventricle, which may then be used to infer a pressure wave due to the atrial contraction. In another example, one or more atrial artifacts may be used to identify the end of passive filling for hemodynamic optimization. For example, passive filling may by typically completed approximately 500 milliseconds after the S2 heart sound. In yet another example, the timing window may be open between the S3 and S4 heart sounds. In some cases, the control module of the LCP may set a decreasing signal threshold to allow smaller signals to reach the input amplifier after the S3 heart sound in order to increase the signal. In some cases, the control module may be configured to run a continuous integration of the pressure signal as a surrogate for pressure, which may then be used to create a timing window. It is contemplated that changes in ventricular filling and/or pressures over time may be used to pick up respiration signals that may be used to support other features of the LCP 100, 400. These are just some examples of how atrial artifacts can be detected by an LCP within the ventricle, which can then be used to identify an atrial timing fiducial for use in timing delivery of a pacing pulse to the ventricle.

It is contemplated that the control module of the LCP 100, 400 may be configured to search for an atrial artifact and identify a search window in more than one manner. In some cases, pacing can cover up, hide, or otherwise distort atrial artifacts and may make then difficult to identify. It may be desirable to allow the LCP to enter a listening mode in which the control circuitry does not issue pacing commands. The listening mode may be for a predefined window of time during a cardiac cycle that is less than the entire cardiac cycle. This may allow the LCP 400 to identify an atrial event without hiding or covering up the atrial artifact of interest (e.g. the A-wave). In some cases, such as when the patient is not pacing dependent, pacing can be paused for a cardiac cycle or two when no atrial activity is detected in order to determine if pacing is covering the atrial artifact(s) if interest. If the patient is pacing dependent, the pacing rate may be slowed (period extended) to allow for a larger period of time to search for the atrial artifacts without a pacing pulse present. Once the atrial artifact has been identified, the LCP may use the artifact to control the timing of the pacing pulse for a one or more cardiac cycles. In the event that an atrial artifact is not found, the LCP may return to its original pacing rate. In some cases, the LCP may be configured to pause or delay pacing and look for an atrial artifact and/or event on a predetermined time schedule.

It is further contemplated that in the event that the atrial artifact is not found the control module may be configured to deliver a pacing therapy at an altered pacing rate. In an example, the altered pacing rate may be less than the pacing rate delivered while atrial events are detected. In another example, the altered pacing rate may be greater than the pacing rate delivered while atrial events are detected. In a further example, the altered pacing rate may be static (e.g., remain constant) during the time there is a failure to detect atrial events. In yet another example, the altered pacing rate may be dynamic (e.g., change) during the time there is a failure to detect atrial events.

In another example, the control module may be configured to switch to a pacing only mode (in some cases a VOO mode). In this example, the control module may be configured to analyze the inputs received from the various sensor modules to determine if some sensors are providing a clearer signal than others. The control module may be configured to prioritize which sensor module is used to search for an atrial artifact and/or event before re-entering VDD mode. When in VOO mode, it may be desirable to pace off of the P-wave. However if this is not possible, it may be desirable to open a timing window based on other sensors including, but not limited to, pressure sensors and/or accelerometers to identify an atrial contraction. It is contemplated that the control module may be configured to switch between sensing modes and pacing modes as needed.

The control module may be configured to determine a quality threshold for a timing window, which may reflect the quality of the atrial artifact signal identified during the timing window. For example, the control module may be configured to analyze or grade a current A-wave timing window. If the current A-wave timing window does not meet certain quality metrics (e.g. percent of cardiac cycles in which an A-Wave is detected, the signal-to-noise ration of the detected A-wave signal, etc.), the control module may discard the window and use a previous window or calculate a new timing window. In some cases, the control module may prioritize one type of atrial artifact over another based on the quality of the detected signal.

As described above, the LCP 100, 400 may use different atrial and/or ventricle artifacts to determine when to search for an artifact and when to open the timing window. The LCP 100, 400 may include a sensing module that includes at least two of a pressure measurement module, an acoustic measurement module, an acceleration measurement module, and an electrogram measurement module. In some cases, the sensing module may include at least a pressure measurement module and at least one of an acoustic measurement module, an acceleration measurement module, and an electrogram measurement module. In some cases, the control module may use a ventricular event such as the R-wave to identify when to start a search window. In some cases, the control module may use different search windows to identify atrial artifacts from different measurement modules. The control module may identify a window of time during each of one or more cardiac cycles in which an atrial artifact and/or atrial event is expected to occur. The window of time may be less than an entire cardiac cycle. The control module may analyze information gathered by the sensing module (e.g., using at least one of the pressure measurement module, an acoustic measurement module, an acceleration measurement module, and an electrogram measurement module) to identify an atrial event (e.g., atrial kick). The control module may then deliver or command a pacing module to deliver a ventricular pacing pulse via the pacing electrodes of the LCP. The ventricular pacing pulse is delivered at a time that is based at least in part on the timing of the identified atrial event. For example, the pacing pulse may be delivered a predetermined length of time (e.g. A-V delay) after the identified atrial event. It is contemplated that the A-V delay that is used may depend on the particular atrial event that was identified. That is, different atrial events may cause different A-V delays to be applied.

The control module may be further configured to average the signals gathered from the sensing module in a similar manner to that described with respect to FIG. 11. For example, the control module may be configured to use signal averaging of the signals gather at the sensing module during each of a plurality of cardiac cycles to determine a signal average. The signal average may then be used to identify a window of time within a cardiac cycle. The identified window of time may then be used in subsequent cardiac cycles to search for and identify an atrial artifact and/or atrial event.

In some cases, the control module may be configured to move the window of time to search for an atrial artifact and/or atrial event. For example, if one of measurement modules of the sensor module is providing a better signal (e.g. better SNR), the control module may base the window around the detected artifact with a clearer signal. As the artifacts can occur at varying time points within the cardiac cycle, the window may be moved accordingly, sometimes cycle-to-cycle. The control module may be configured to select which measurement module to use dynamically or on a case to case basis.

In some cases, the control module may use different quality measurements to determine which measurement module to use. For example, the control module may select the measurement module with a better Signal-to-Noise Ratio (SNR). In another example, a p-wave detecting atrial activation by an electrogram measurement module may have a higher priority than a pressure signal detecting an atrial kick by a pressure measurement module. However, due to the inability of a ventricle only configuration to reliably sense a P-wave, the LCP may not rely solely on the P-wave to identify an atrial artifact and/or event. It may in fact, it may switch to detecting the A-wave when the P-wave is not available, and/or may use the A-wave to confirm the detection of a noisy P-wave. These are just examples.

In some cases, the control module may combine information gathered from more than one measurement module in identifying an atrial artifact and/or atrial event. For example, the control module may use both pressure data and electrocardiogram data in identifying an atrial artifact and/or event. In some cases, when data is used from two or more measurement modules, the data from each measurement module may be weighted differently (e.g., one may count more or be weighted more heavily than another). It is further contemplated that the control module may be configured to lengthen the window (e.g., make it longer) under certain conditions. For example, the window may not be long enough to identify an atrial artifact and/or event or a pacing pulse may be covering up the atrial event. In other cases, the window may be shortened (e.g., when noise is present, the noise may be reduced with a shortened window).

Figure 13:
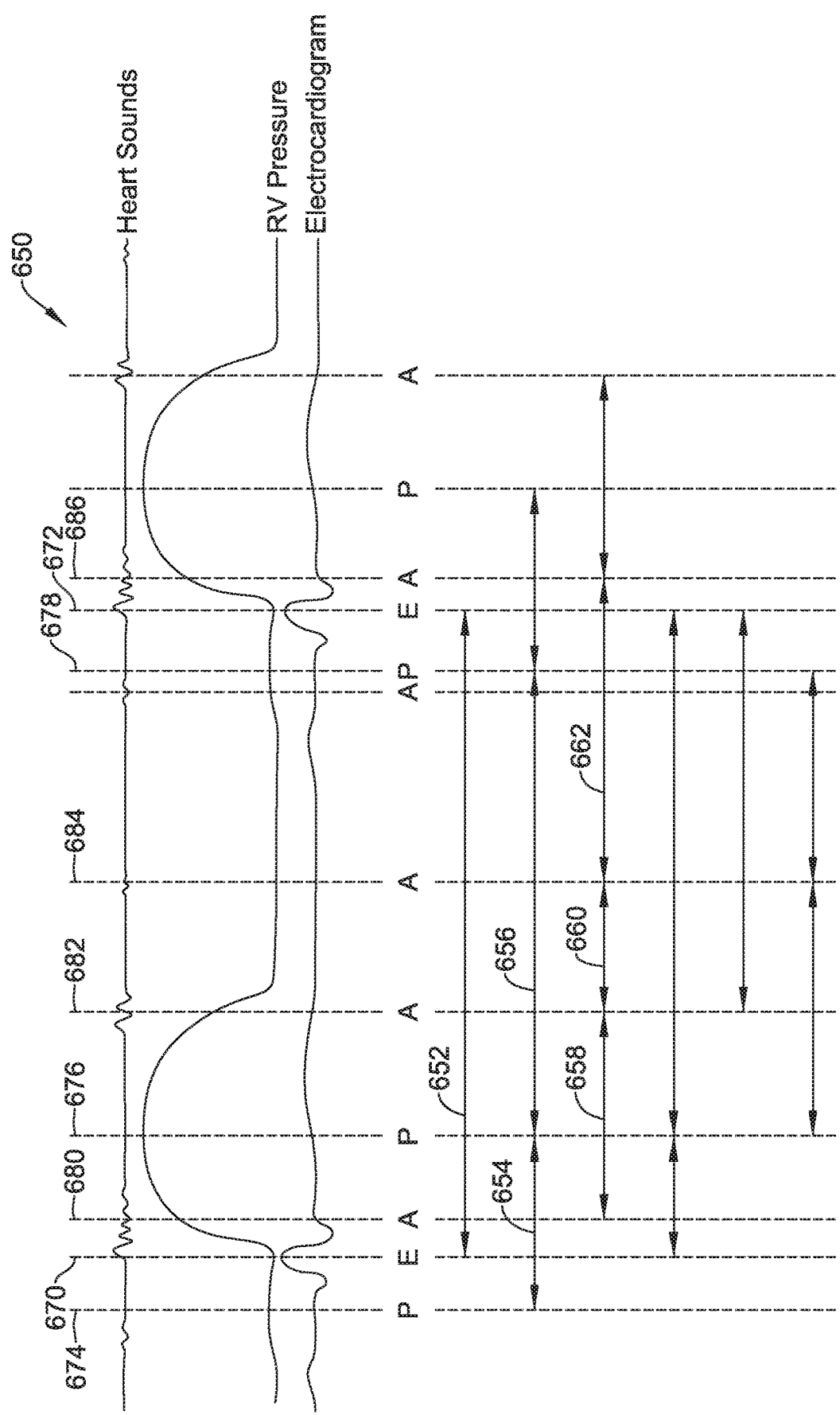
FIG. 13 shows a graph of illustrative cardiac signals including heart sounds, right ventricular pressure, and an electrocardiogram, along with various intervals between detectable characteristics of such signals.

As described herein, the timing intervals for both searching and pacing may be based on pressure and/or heart sound fiducials (as well as other atrial artifacts described herein) as opposed to basing the intervals off solely of an electrocardiogram. FIG. 13 is a graph 650 of illustrative cardiac signals including heart sounds, right ventricular pressure, and an electrocardiogram. FIG. 13 also shows various intervals between various artifacts of these signals. It is contemplated that a number of different artifacts or characteristics during a cardiac cycle can be used to form a number of different timing intervals. For example, there can be intervals that extend between two electrocardiogram signals (E-E) such as between an R-wave amplitude 670 of a first cardiac cycle and an R-wave amplitude 672 of the next cardiac cycle, as indicated at arrow 652. Another interval may be defined between two pressure signals (P-P), such as between an A-wave pressure 674 and a maximum systolic pressure 676 of the same cardiac cycle, as shown at arrow 654, or between a maximum systolic pressure 676 of a first cardiac cycle and an A-wave pressure 678 in the subsequent cardiac cycle, as shown at arrow 656. Another illustrative interval may be defined between two acoustic signals (A-A), such as between an S1 heart sound 680 and an S2 heart sound 682, as shown at arrow 658, between an S2 heart sound 682 and an S3 heart sound 684 as shown at arrow 660, and/or between an S3 heart sound 684 and an S1 heart sound 686 of a subsequent cardiac cycle, as shown at arrow 662.

As illustrated in FIG. 13, there can also be intervals defined between an electrocardiogram signal and a pressure signal (E-P), between a pressure signal and an electrocardiogram signal (P-E), between an electrocardiogram signal and an acoustic signal (E-A), between an acoustic signal and an electrocardiogram signal (A-E), between a pressure signal and an acoustic signal (P-A), and/or between an acoustic signal and a pressure signal (A-P). It is contemplated that any measurable parameter may serve as the beginning and/or end of an interval as desired, and the intervals are not limited to those explicitly described or shown in FIG. 13.

Figure 14:
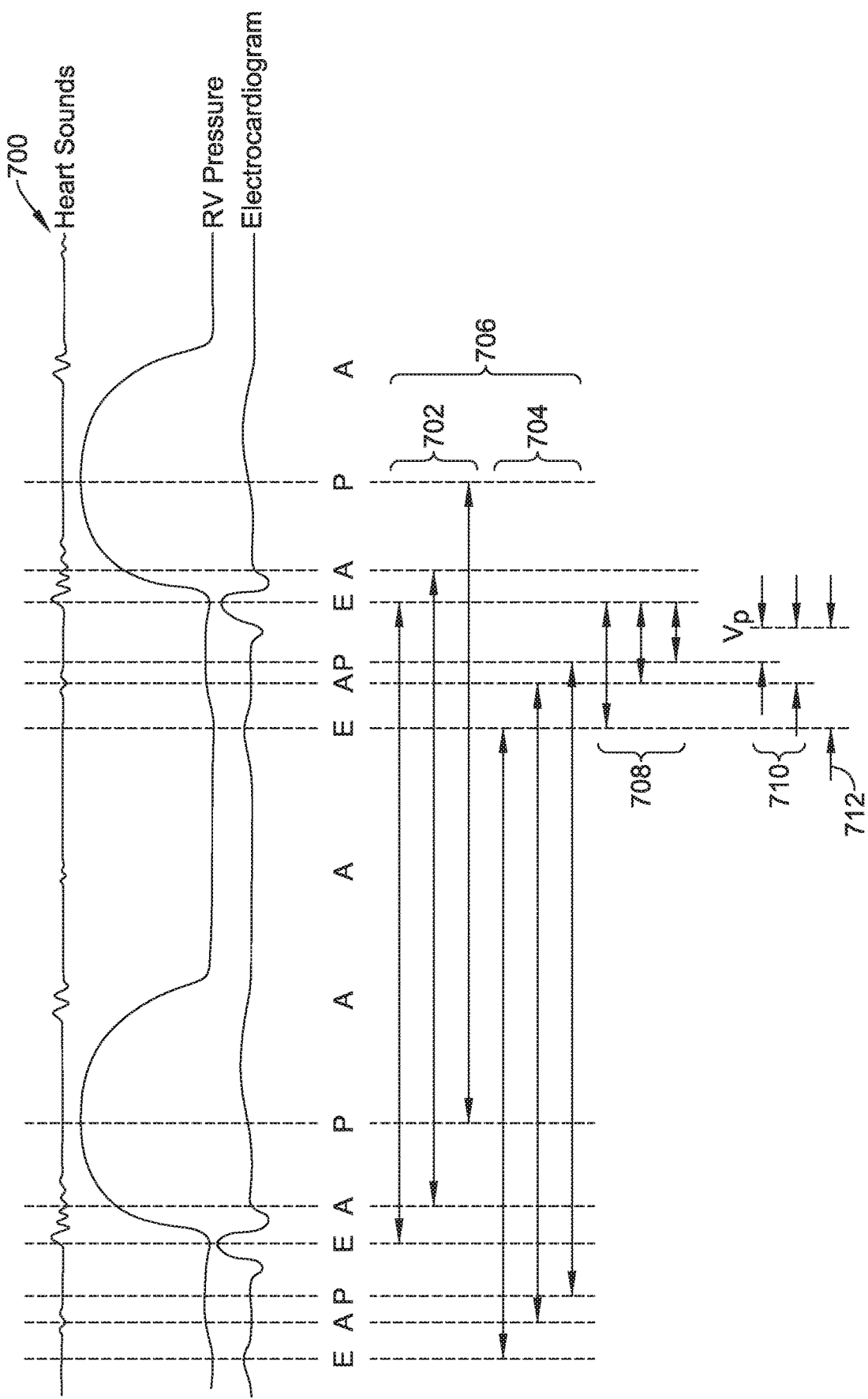
FIG. 14 shows a graph of illustrative cardiac signals including heart sounds, right ventricular pressure, and an electrocardiogram, along with various timing delays (AV intervals) from detectable characteristics of such signals to a desired ventricle pacing pulse.

FIG. 14 is a graph 700 of illustrative cardiac signals including heart sounds, right ventricular pressure, and an electrocardiogram. FIG. 14 also shows various intervals between various artifacts of these signals. As described herein, there can be a number of different intervals using various sensed parameters. Not only can there be various intervals from a sensed artifact to another sensed artifact, but also various intervals from a sensed artifact to a pacing pulse.

The E-E (R-wave to subsequent R-wave), A-A (S1 to subsequent S1), and P-P (max pressure to subsequent max pressure) intervals shown at 702 are three ventricular intervals. The E-E (P-wave to subsequent P-wave), A-A (S4 to subsequent S4), and P-P (atrial kick to subsequent atrial kick) intervals shown at 704 are three atrial intervals. These intrinsic same chamber intervals 706 have the same or roughly the same time interval between same sensed artifacts or events regardless of which parameter is used (e.g., R-wave to R-wave, S1 to S1, max pressure to max pressure). In contrast, intervals between chambers 708 vary substantially. As can be seen at 708 in FIG. 14, atrioventricular (A-V) intervals vary significantly depending on which atrial event is selected for the atrial timing fiducial. An E-E (P-wave to R-wave) interval, A-E (S4 to R-wave), and P-E (atrial kick to R-wave) intervals shown at 708 are three illustrative atrioventricular (AV) intervals each having a different duration. The duration of each of these AV intervals can be sensed during one or more intrinsic heart beats (e.g. no pacing). In some cases, the duration of each of these intervals can be sensed during a plurality of intrinsic heart beats (no pacing) and then averaged, resulting in an average AV interval for each of the different atrial timing fiducials as shown at 710.

As described above, a P-wave may not be consistently detected in a device implanted in the ventricle. As such, it may be desirable to time the ventricular pacing pulse (Vp) using a pressure artifact (e.g., a-wave or atrial kick) as the atrial timing fiducial along with a corresponding AV interval.

In some cases, it may be desirable for the LCP 100, 400 to be configured to operate in a number of different pacing modes. Some illustrative pacing modes may include, but are not limited to VDD, VDDR, VVI, VVIR, VOO, and VOOR. As used herein, the pacing modes use the North American Society of Pacing and Electrophysiology (NASPE) and British Pacing and Electrophysiology Group (BPEG) pacemaker codes as outlined in Table 1 below:

TABLE 1

| NASPE/BPEG Revised in 2002 NBG Pacemaker Code | | | | |
|---|---|---|---|---|
| Position I | Position II | Position III | Position IV | Position V |
| (Chamber Paced) | (Chamber Sensed) | (Response to Sensed Event) | (Programmability, Rate Modulation) | (Multisite Pacing) |
| O = none | O = none | O = none | | O = none |
| A = atrium | A = atrium | I = inhibited | | A = atrium |
| V = ventricle | V = ventricle | T = triggered | O = none | V = ventricle |
| D = dual (A + V) | D = dual (A + V) | D = dual (T + I) | R = rate moduation | D = dual (A + V) |

Miller RD. Miller's Anesthesia, 6$^{th}$ ed. Philadelphia: Elsevier, Inc, 2005, pp 1417.

In another example, it may be desirable to time the ventricular pacing pulse (Vp) using an acoustic artifact (e.g., S4) as the atrial timing fiducial along with a corresponding AV interval. The corresponding AV interval used with an acoustic artifact (e.g., S4) may be different than the AV interval used with a pressure artifact, as seen at 710 in FIG. 14. In yet another example, it may be desirable to time the ventricular pacing pulse (Vp) using an electrical artifact (e.g., P-wave) as the atrial timing fiducial along with a corresponding AV interval, as seen at 712 in FIG. 14. These are just examples. The LCP may dynamically switch between these and other atrial timing fiducials, depending on a number of factors such as the quality of the signals that are currently sensed. In some cases, an atrial timing fiducial may be determined from two or more cardiac artifacts, sometimes with one weighted more than the others.

The sensing module of the LCP 100, 400 may include one or more of a pressure measurement module and an acoustic measurement module. However, other measurement modules may be used as desired, including but not limited to, measurement modules that include suitable sensors for determining the artifacts described with respect to FIGS. 6 and 7. For example, the sensing module may further include an electrogram measurement module. As described herein, the sensing module may be configured to gather information suitable for determining one or more atrial timing fiducials. The information may include, but is not limited to, an atrial artifact such as any of those discussed with reference to FIGS. 6 and 7. In some cases, information gathered from one of the measurement modules may be used to determine a blanking interval for another measurement module.

In some cases, a pressure measurement module may detect or determine at least one of a maximum pressure (atrial or ventricular), a minimum pressure (atrial or ventricular), a mean pressure (atrial or ventricular), a pressure time integral (atrial or ventricular), and/or a pressure time derivative (atrial or ventricular). An acoustic measurement module may detect or determine at least one of an S1 heart sound, an S2 heart sound, an S3 heart sound, and/or an S4 heart sound. An acceleration measurement module, if present, may detect or determine at least of an S1 heart sound, an S2 heart sound, an S3 heart sound, an S4 heart sound, myocardial (e.g., heart wall) movement, patient activity and/or patient posture. These and other artifacts may be used as the basis for an atrial timing fiducial.

A VDD device is a device pacing in the ventricle, sensing both the atrium and the ventricle, and using triggered and inhibited pacing.

It is contemplated that a right ventricle LCP 100, 400 using remote tracking of atrial activity such as described herein may automatically revert from one pacing mode to another, depending on one or more sensed conditions. The reversionary behavior may be desirable for safe operation and/or for enhancing the effectiveness of the pacing therapy. The control module may be configured to search for and identify conditions that may indicate a reversion is desirable. Some conditions may include, but are not limited to: an atrial artifact (e.g., atrial timing fiducial) occurring too close to the R-wave (or other ventricular fiducial); a hemodynamic response that indicates that the present pacing therapy is worse than another pacing therapy or no pacing therapy, either actual or anticipated (due to one or more of posture, heart rate, respiratory rate, respiratory cycle, patient activity, physiological noise, environmental noise, etc.); continuous or intermittent loss of an atrial tracking artifact or fiducial; actual or anticipated continuous or intermittent loss of an atrial tracking artifact or fiducial due to search algorithms associated with reacquiring an atrial artifact or fiducial; a time period between adjacent atrial artifacts or fiducials being too short (e.g., due to over sensing caused by physiological or environmental noise or atrial tachyarrhythmia); and/or a ventricular interval being too short (e.g., due to over sensing caused by physiological or environmental noise or ventricular tachyarrhythmia). These are just some examples. Other events and conditions may be detected and cause reversionary behavior.

The LCP 100, 400 may experience or be configured to use different types of reversionary behavior based on the current conditions. In a first example, the control module may be configured to change pacing modes. In the event of a loss of an atrial timing fiducial, an atrial rate above a specified threshold, or atrial noise above a threshold, the LCP may be configured to automatically switch between VDD and VVI modes. In the event of ventricular noise being above a threshold, the LCP may be configured to automatically switch between VDD or VVI and VOO modes. In the event of a reduction in the hemodynamic signal, the LCP may be configured to automatically switch between VDD or VVI and OOO modes.

In an example LCP 100, 400 reverts to a VDI mode wherein the device continues to search and/or measure atrial artifacts but does not use any detected atrial artifacts to trigger ventricular pacing. If the LCP determines the atrial fiducial can be reliably determined the LCP reverts back to a mode that allows triggering of ventricular paces from the atrial fiducial (e.g. VDD mode).

In some cases, the control module may be configured to manipulate the tracking algorithm. For example, the control module may switch between continuous tracking and intermittent tracking with tracking estimate and search. In yet another example, the atrial timing fiducial signal may be reverted. In another example, the type of signal and/or portion of signal used to determine the atrial timing fiducial may be changed or switched. In yet another example, the atrial timing fiducial may be changed from a first weighted average of two or more signals to a second different weighted average of the same or different two or more signals. These are just examples.

Figure 15:
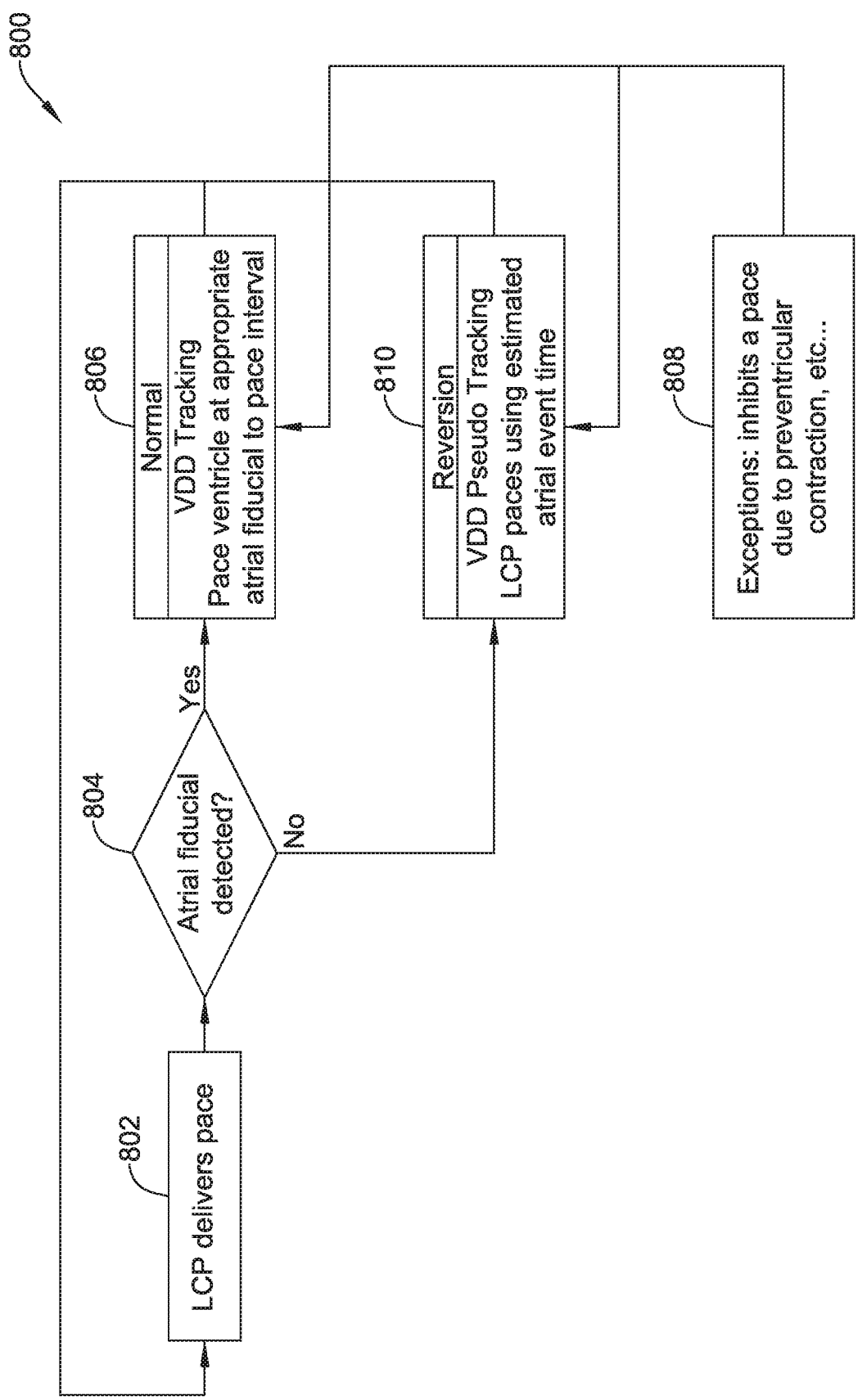
FIG. 15 is an illustrative method for determining when a medical device should utilize reversion.

FIG. 15 is a flow chart 800 of an illustrative method for determining whether the LCP 100, 400 should utilize reversion. The control module may continuously verify the current pacing mode is the best under the current conditions. If a reversion is needed, the control module may dynamically change the pacing mode (e.g., change on a beat-to-beat basis, if needed). The LCP 100, 400 may first deliver a pace, as shown at 802. After delivering the pace, the control module may check to see if the atrial artifact and/or event (e.g., atrial timing fiducial) was detected, as shown at 804. If the atrial timing fiducial was detected, the LCP 100, 400 may continue with its normal operational mode, which in some cases may be VDD tracking with the pacing occurring after the corresponding AV interval, as shown at 806. An exception may occur when the normal VDD tracking inhibits a pacing pulse due to preventricular contraction, as shown at 808. If the atrial timing fiducial was not detected or resolved, the LCP 100, 400 may enter a reversionary mode, as shown at 810. In some cases, in the reversionary mode, the LCP 100, 400 may enter a VDD pseudo tracking mode in which the LCP 100, 400 paces using an estimated atrial timing fiducial time. Other reversionary modes may be used as appropriate. The control module may be configured to select a ventricular pacing therapy and/or mode based at least in part on one or more of the tracked atrial artifacts/ events. In some cases, a first ventricular pacing therapy may have a first pacing rate and the reversionary (or second) ventricular pacing therapy may have a second pacing rate different from the first. For example, the reversionary ventricular pacing therapy may extend the pacing rate to aid in the search for the atrial timing fiducial.

Figure 16:
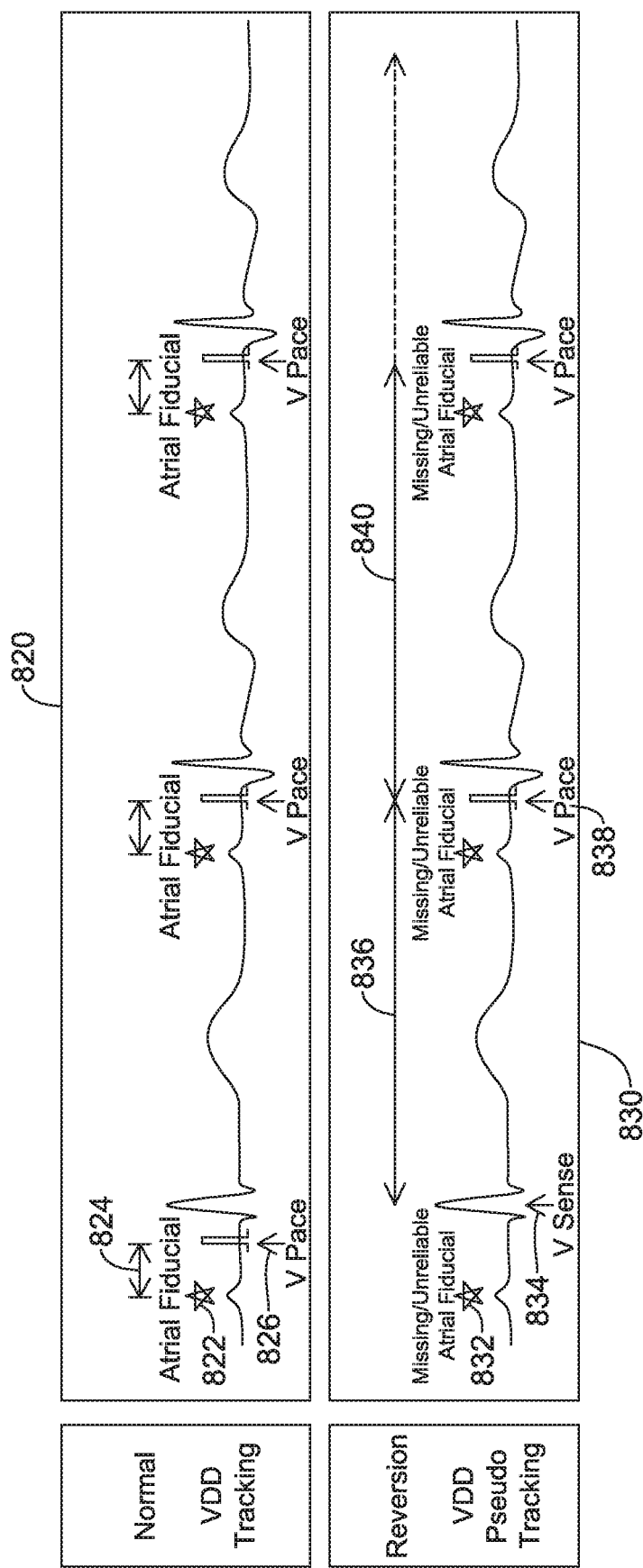
FIG. 16 illustrates a comparison of pacing intervals on an electrocardiogram when the device is operating in a normal VDD tracking mode and pacing intervals on an electrocardiogram when the device is operating in a VDD pseudo tracking mode.

FIG. 16 illustrates a comparison of pacing intervals on an electrocardiogram when the LCP 100, 400 is operating in a normal VDD mode 820 and pacing intervals on an electrocardiogram when the LCP 100, 400 is operating in a VDD pseudo tracking mode 830. As can be seen in the normal VDD mode 820, the control module is detecting an atrial timing fiducial 822, and using the appropriate AV delay 824, delivers the pacing pulse 826 at the appropriate time. The LCP 100, 400 will continue to operate in this manner unless conditions change that make VDD pacing unsafe or less desirable.

FIG. 16 illustrates an example in which the control module of the LCP 100, 400 has determined that the atrial artifact/event 832 is missing or unreliable. The control module may then sense a ventricular event 834 (such as but not limited to the R-wave) and essentially use the ventricular event 834 as the atrial pacing fiducial for the next cardiac cycle. The control module may determine an appropriate AV interval 836, calculated using the ventricular intrinsic interval (e.g., R-wave to subsequent R-wave) minus a previously stored pace to R wave interval. In the example shown, starting at the sensed ventricular event 834, the pacing pulse 838 may be delivered at a time equal to the R-wave to R-wave intrinsic interval minus a percentage of the historical AV interval. It is contemplated that the percentage of the historical AV interval may be in the range of about 30 to 70%. Alternatively, a fixed time period, such as, but not limited about 200 milliseconds may be used in place of the percentage of the historical AV interval or a previously stored pace to R wave interval. The control module may then continue to pace using the R-wave to R-wave intrinsic interval 840 as the timing interval using the pacing pulse 838 as the timing fiducial until a suitable atrial timing fiducial is identified. If the control module fails to re-acquire a suitable atrial timing fiducial, the control module may command the device to enter a search mode in an attempt to detect an intrinsic atrial and/or ventricular event. This is just one example of a reversionary scenario.

The control module may be configured to determine the accuracy of the atrial timing fiducial by analyzing the effectiveness of the pacing therapy. In one example, the control module may use the upstroke (e.g., dP/dt or peak pressure) on sequential cardiac cycles to estimate the accuracy of the A-wave detection. If the LCP 100, 400 is pacing at an incorrect time due to an inaccurate atrial timing fiducial, passive filling may be reduced thereby reducing the dP/dt. Similarly, the control module may use an integrator to find the area under the pressure waveform, which may represents the filling volume of the ventricle, or impedance between the electrodes of the LCP may be used as an indication of ventricle volume. Poor filling volume may indicate an inaccurate atrial timing fiducial. In yet another example, the control module may be configured to search for edges using, for example a high-pass pole to create a differentiator to help identify a sub-par atrial timing fiducial. If the atrial timing fiducial is determined to be inaccurate, the LCP may revert to asynchronous pacing (e.g. VOO mode). Alternatively, if the patient's intrinsic heart rate is high enough (e.g. 50 BPM), the LCP may revert to no pacing (e.g. OOO mode).

Figure 17:
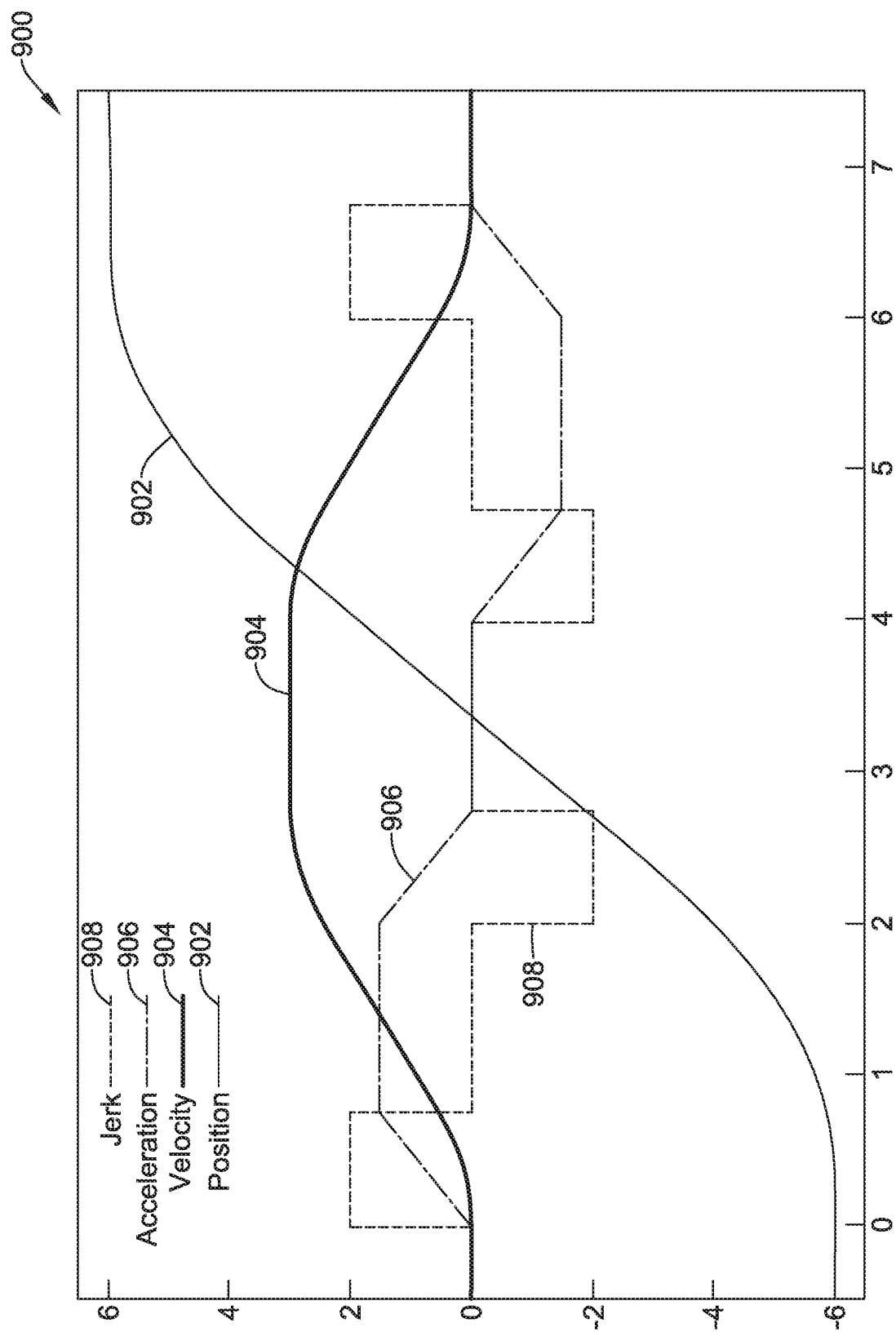
FIG. 17 is a graphic representation of higher order derivatives that can be used by an LCP implanted in the ventricle to help identify atrial timing fiducials.

In addition to a first-order differentiator, higher-order differentiation could further provide better timing fiducials (e.g., more crisp) and other measures such as verification of signal quality. A third order time derivative of position is known as "jerk", which is the change in acceleration with respect to time. FIG. 17 illustrates a graph 900 of an illustrative relationship of higher order differentiation of a signal 902. The signal 902 could be any suitable signal including an egram, a pressure signal, an acceleration signal, or any other suitable signal. The change in pressure with respect to time may be considered the first derivative 904. The change in the first derivative 904 with respect to time may be considered the second derivative 906. The change in second derivative with respect to time may be considered as an equivalent to jerk 908 (or the third derivative). When the signal is a pressure signal, the inflections produced by an A-wave may give third order blips which could be used for timing or verifying a quality of the signal.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

The invention claimed is:

1. A leadless cardiac pacemaker (LCP) configured to sense cardiac activity and to deliver pacing therapy to a ventricle of a patient's heart, the LCP comprising:
   a housing having a proximal end and a distal end;
   a first electrode secured relative to the housing and exposed to the environment outside of the housing;
   a second electrode secured relative to the housing and exposed to the environment outside of the housing;
   a sensing module disposed within the housing, the sensing module configured to:
      detect a first atrial artifact during a heartbeat;
      detect a second atrial artifact during the same heartbeat, wherein the second atrial artifact is different from the first atrial artifact;
      determine an atrial timing fiducial based at least in part on both the detected first atrial artifact and the detected second atrial artifact; and
   circuitry in the housing operatively coupled to the first electrode and the second electrode, and also operatively coupled to the sensing module, the circuitry configured to deliver a ventricular pacing therapy to the patient's heart via the first electrode and the second electrode, wherein the ventricular pacing therapy is time dependent, at least in part, on the atrial timing fiducial determined by the sensing module.

2. The LCP of claim 1, wherein the sensing module is configured to sense at least one of a pressure, impedance, strain, sound, rotation, acceleration, voltage, and flow.

3. The LCP of claim 1, wherein the first atrial artifact and/or the second atrial artifact comprises at least one of a p-wave, S2 heart sound, S3 heart sound, tricuspid valve position, mitral valve position, and akinetic ventricular pressure.

4. The LCP of claim 1, wherein the first atrial artifact and/or the second atrial artifact comprises a transition between passive and active ventricular filling.

5. The LCP of claim 1, wherein the circuitry is configured to determine an intrinsic interval based, at least in part, on two or more atrial timing fiducials determined by the sensing module.

6. The LCP of claim 1, wherein the sensing module comprises:
   a first sensor having a first sensor type, wherein the first sensor is configured to sense the first atrial artifact; and
   a second sensor having a second sensor type, the second sensor is configured to sense the second atrial artifact, wherein the second sensor type uses a different sensing modality than the first sensor type.

7. The LCP of claim 6, wherein the first sensor comprises an accelerometer and the second sensor comprises a pressure sensor.

8. The LCP of claim 1, wherein the sensing module comprises a single sensor that is configured to detect the first atrial artifact and the second atrial artifact.

9. The LCP of claim 1, wherein the first atrial artifact comprises an S2 heart sound and the second atrial artifact comprises an S4 heart sound.

10. The LCP of claim 1, wherein the first atrial artifact comprises either an S2 heart sound or an S4 heart sound and the second atrial artifact comprises an A wave.

11. An implantable medical device configured to sense cardiac activity and to deliver pacing therapy to a patient's heart, the implantable medical device comprising:
    a housing;
    a first electrode secured relative to the housing and exposed to the environment outside of the housing;
    a second electrode secured relative to the housing and exposed to the environment outside of the housing;
    a sensing module disposed within the housing, the sensing module comprising:
       a first sensor having a first sensor type configured to detect a first atrial artifact during a heartbeat;
       a second sensor having a second sensor type configured to detect a second atrial artifact during the same heartbeat, wherein the second sensor type uses a different sensing modality than the first sensor type;
       the sensing module is configured to determine an atrial timing fiducial based at least in part on both the first atrial artifact detected by the first sensor and the second atrial artifact detected by the second sensor; and
    circuitry in the housing operatively coupled to the first electrode, the second electrode, and the sensing module, the circuitry configured to deliver a ventricular pacing pulse to the patient's heart via the first electrode and the second electrode, wherein a timing of the ventricular pacing pulse is dependent, at least in part, on the timing of the atrial timing fiducial determined by the sensing module.

12. The implantable medical device of claim 11, wherein the sensing module comprises a filter for filtering a sensor output from the first sensor to help identify and detect the first atrial artifact.

13. The implantable medical device of claim 12, wherein the filter includes a first filter for passing a first frequency band of the sensor output, a second filter for passing a second frequency band and a third filter for passing a third frequency band.

14. The implantable medical device of claim 11, wherein the sensing module is configured to calculate an ensemble average timing over multiple heart beats for the detected first atrial artifact.

15. The implantable medical device of claim 11, wherein the detected first atrial artifact comprises at least one of a p-wave, S2 heart sound, S3 heart sound, tricuspid valve position, mitral valve position, and akinetic ventricular pressure.

16. The implantable medical device of claim 11, wherein the implantable medical device is configured to be implantable in a ventricle of the patient's heart.

17. An implantable medical device configured to sense cardiac activity and to deliver pacing therapy to a patient's heart, the implantable medical device comprising:
    a housing;
    a first electrode secured relative to the housing and exposed to the environment outside of the housing;
    a second electrode secured relative to the housing and exposed to the environment outside of the housing;
    a sensing module disposed within the housing, the sensing module configured to:
       during a heartbeat, sense during ventricular filling of the patient's heart a first atrial artifact using a first sensor;
       during the same heartbeat, sense during ventricular filling of the patient's heart a second atrial artifact using the first sensor, wherein the second atrial artifact is distinct from the first atrial artifact; and determine an atrial timing fiducial based, at least in part, on both the first atrial artifact and the second atrial artifact; and circuitry in the housing operatively coupled to the first electrode, the second electrode, and the sensing module, the circuitry is configured to deliver a ventricular pacing therapy to the patient's heart via the first electrode and the second electrode, wherein the ventricular pacing therapy is time dependent, at least in part, on the identified atrial timing fiducial.

18. The implantable medical device of claim 17, wherein the sensing module comprises a bandpass filter of about 1 Hertz (Hz) to about 5 Hz to identify the first atrial artifact.

19. The implantable medical device of claim 17, wherein the sensing module comprises a bandpass filter of about 15 Hertz (Hz) to about 30 Hz to identify the first atrial artifact.

20. The implantable medical device of claim 17, wherein the implantable medical device is configured to be implantable in a ventricle of the patient's heart.

* * * * *